United States Patent [19]

Shiotani et al.

[11] Patent Number: 5,243,067

[45] Date of Patent: Sep. 7, 1993

[54] PROCESS OF PRODUCTION OF 3,4,3',4'-SUBSTITUTED BIPHENYL COMPOUND

[75] Inventors: Akinori Shiotani; Michinori Suzuki; Fumio Matsuo, all of Ichihara, Japan

[73] Assignee: Ube Industries, Ltd., Yamaguchi, Japan

[21] Appl. No.: 655,361

[22] PCT Filed: Apr. 25, 1990

[86] PCT No.: PCT/JP90/00537

§ 371 Date: Feb. 20, 1991

§ 102(e) Date: Feb. 20, 1991

[87] PCT Pub. No.: WO91/02713

PCT Pub. Date: Mar. 7, 1991

[30] Foreign Application Priority Data

Aug. 18, 1989 [JP] Japan .................................. 1-211334

[51] Int. Cl.$^5$ .................. C07C 67/475; C07C 51/09; C07C 51/60

[52] U.S. Cl. ........................................ 560/96; 560/76; 562/480; 562/481; 562/483; 562/488; 562/855

[58] Field of Search .................... 560/76, 96; 562/481, 562/488, 483, 480, 855

[56] References Cited

U.S. PATENT DOCUMENTS

| | | | |
|---|---|---|---|
| 2,508,022 | 5/1950 | Gluesenkamp | 562/480 |
| 2,809,210 | 10/1957 | Short et al. | 562/480 |
| 4,174,447 | 11/1979 | Fields | 560/76 X |
| 4,288,588 | 9/1981 | Donohue | 560/76 X |
| 4,294,976 | 10/1981 | Itatani et al. | 560/76 |
| 4,338,456 | 7/1982 | Itatani et al. | 560/96 |
| 4,581,469 | 4/1986 | Itatani et al. | 560/96 |
| 4,582,925 | 4/1986 | Donohue | 560/76 |
| 4,727,185 | 2/1988 | Shoji et al. | 562/481 |

OTHER PUBLICATIONS

*Chemical Abstracts*, vol. 78, No. 4, Entry 17644w, (1972).

*Chemical Abstracts*, vol. 81, No. 6, Entry 27069p, (1973).
*Chemical Abstracts*, vol. 81, No. 12, Entry 65068v, (1973).
*Chemical Abstracts*, vol. 81, No. 24, Entry 153492j, (1973).
*Chemical Abstracts*, vol. 83, No. 2, Entry 11181z, (1974).
*Chemical Abstracts*, vol. 87, No. 5, Entry 39127t, (1977).

*Primary Examiner*—Jose G. Dees
*Assistant Examiner*—Vera C. Clarke
*Attorney, Agent, or Firm*—Finnegan, Henderson, Farabow, Garrett & Dunner

[57] ABSTRACT

A 3,4,3',4'-substituted biphenyl compound represented by the general formula (II):

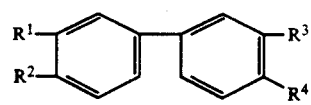

wherein, one of $R^1$ and $R^2$ is a -$CH_3$ group and the one other is a —$COOR^5$ group, —COOH group, or —COCl group, and one of $R^3$ and $R^4$ is a -$CH_3$ group and the other one is a —$COOR^5$ group, —COOH group, or —COCl group, is produced by the steps of oxidatively coupling an o-toluic acid alkyl ester in the presence of a catalyst containing a mixture of palladium salts with 1,10-phenanthroline or α,α'-bipyridine, a chelating product of a palladium salt with 1,10-phenanthroline, or a chelating products of a palladium salt with α,α'-bipyridine, in an atmosphere containing molecular oxygen, to selectively produce a 3,4,3,'4'-substituted dimethyl biphenyl dicarboxylic acid dialkyl esters having a biphenyl ring structure; optionally converting this dialkyl ester compound to a corresponding dimethyl biphenyl dicarboxylic acid, and then optionally further converting this to a corresponding dimethyl biphenyl dicarboxylic acid dichloride.

18 Claims, 27 Drawing Sheets

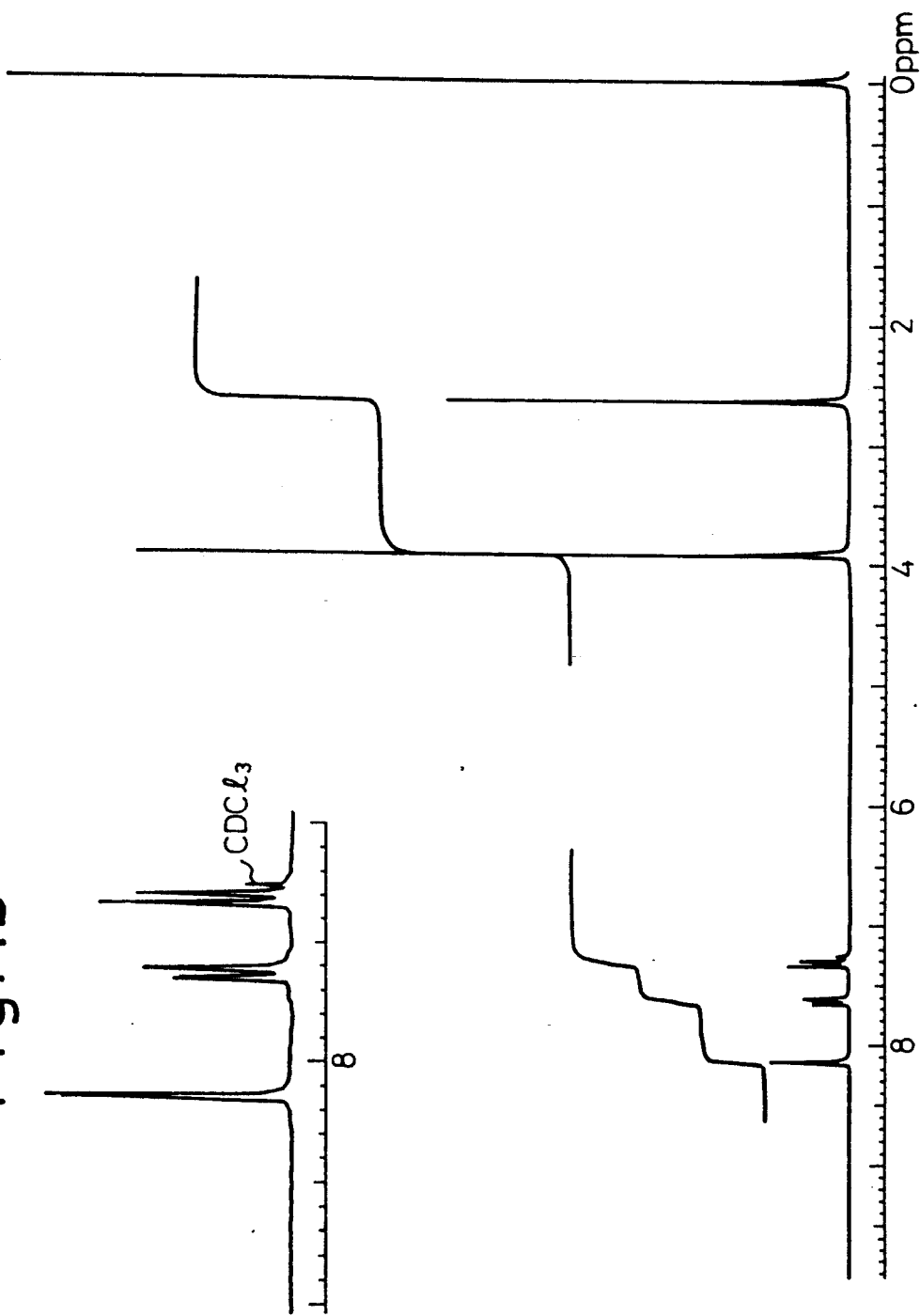

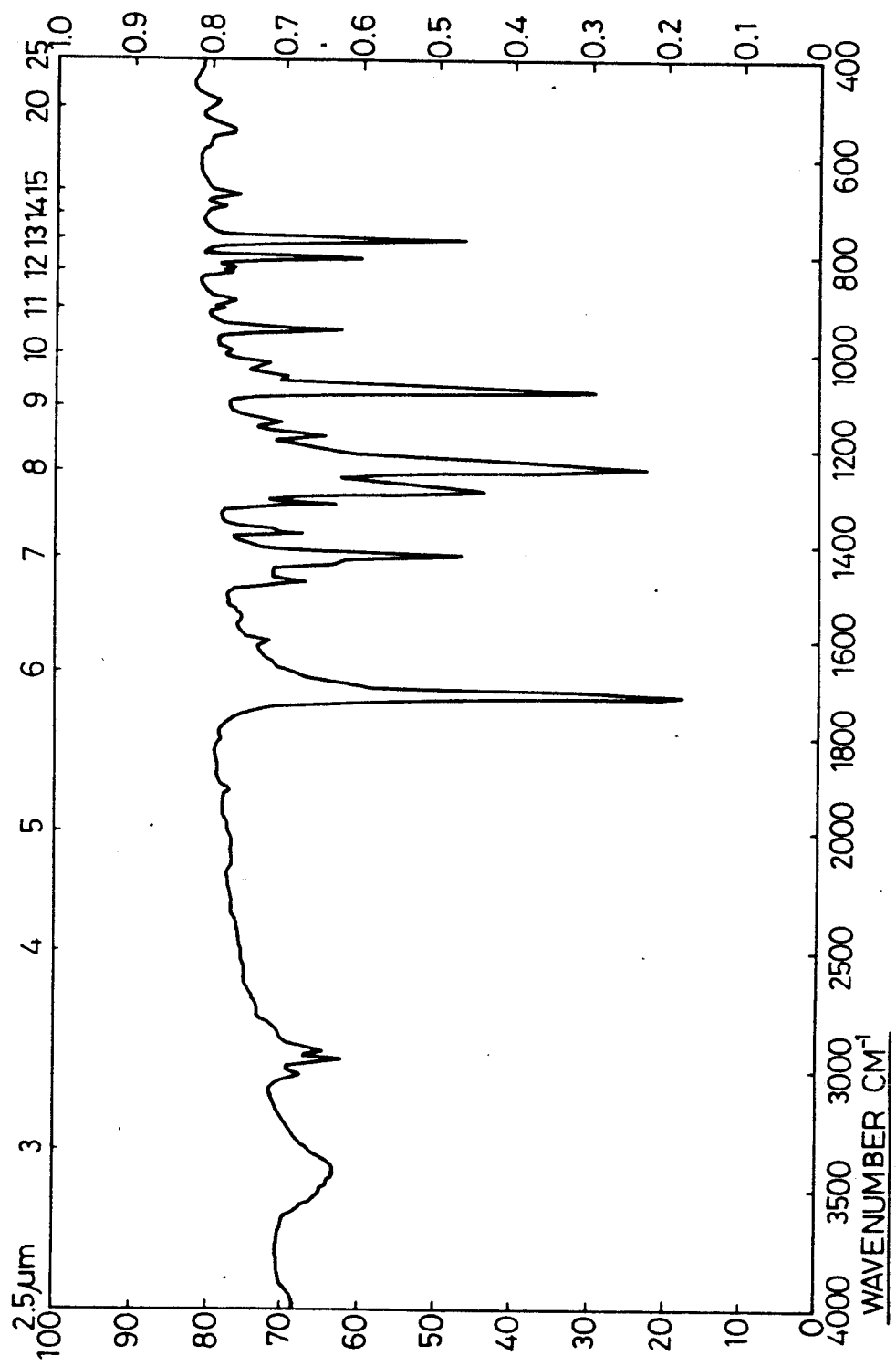

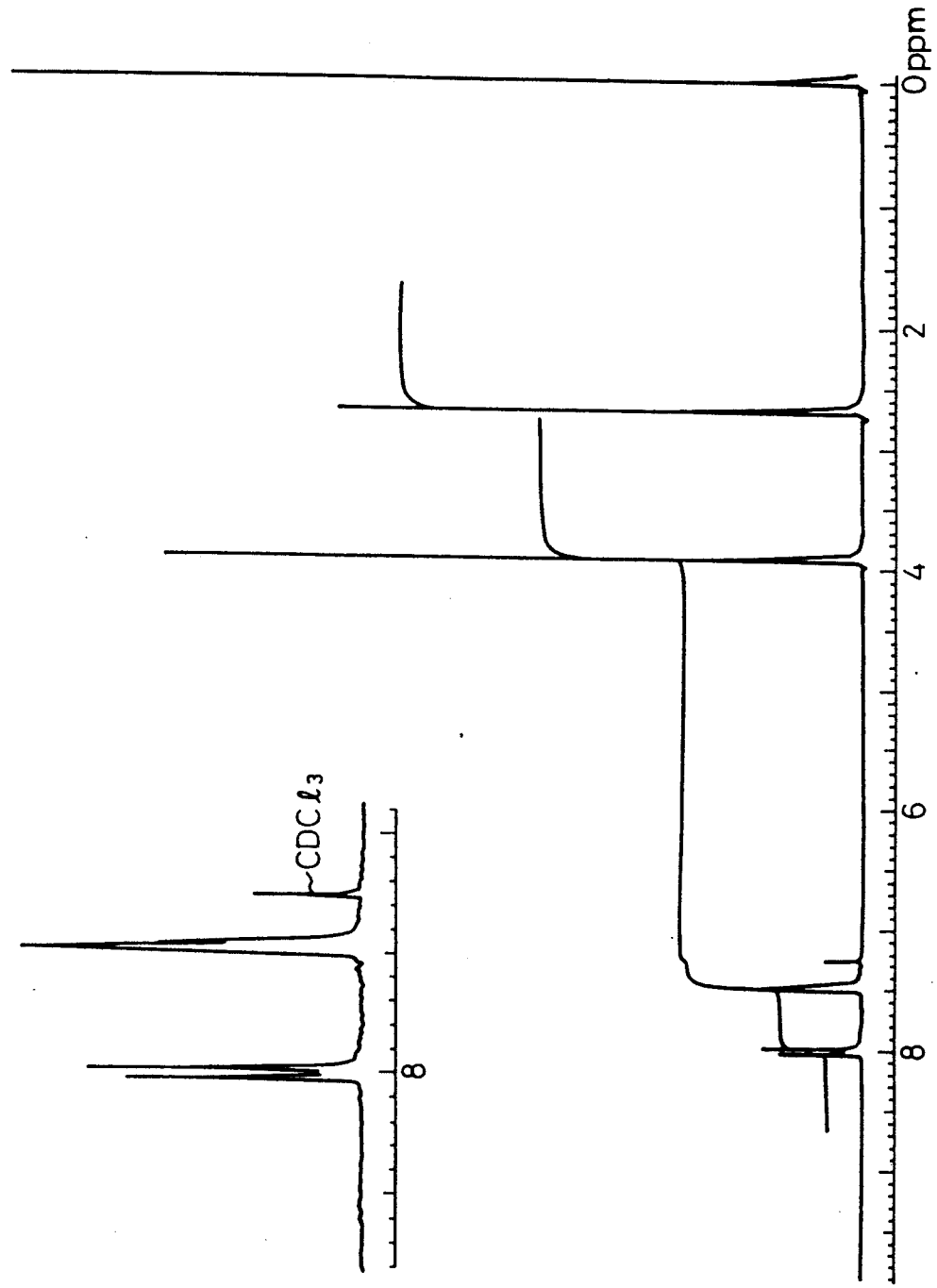

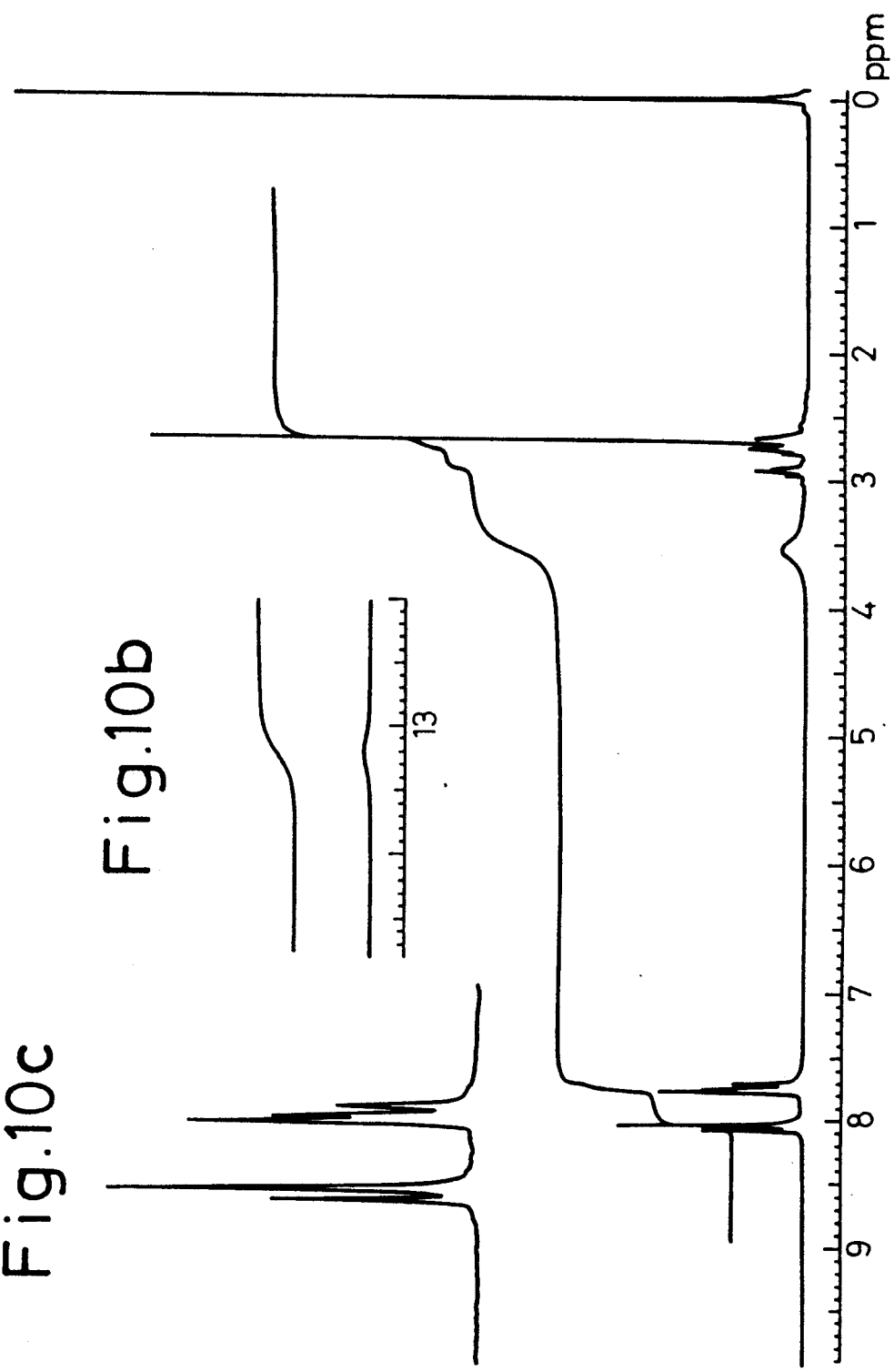
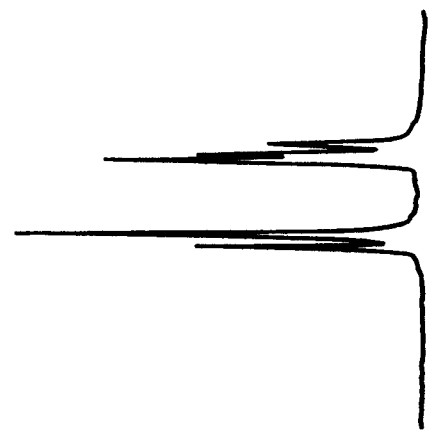
Fig.10a
Fig.10b
Fig.10c

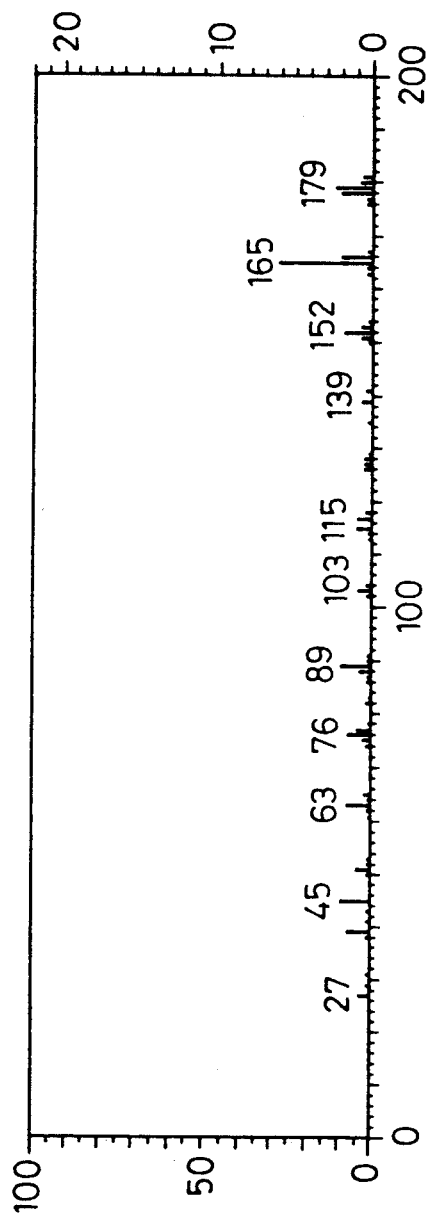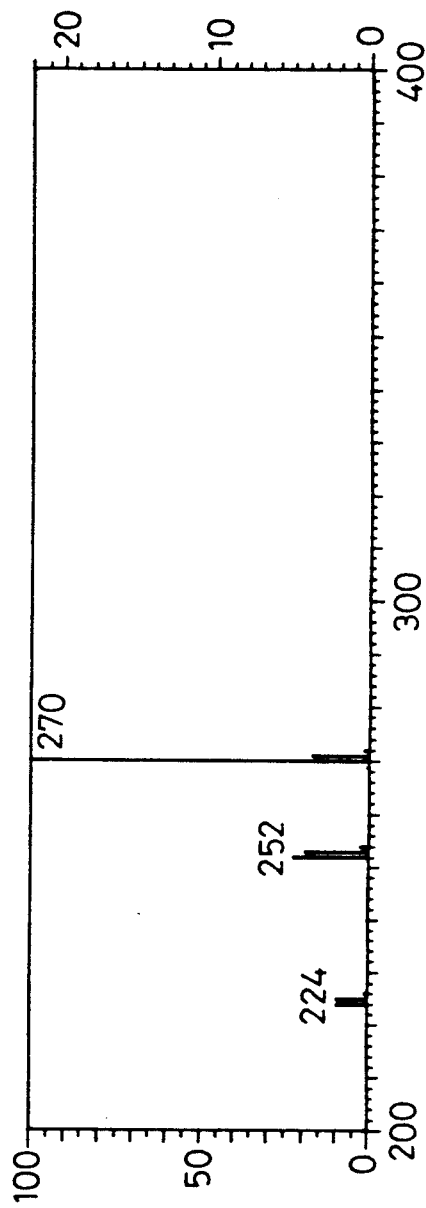

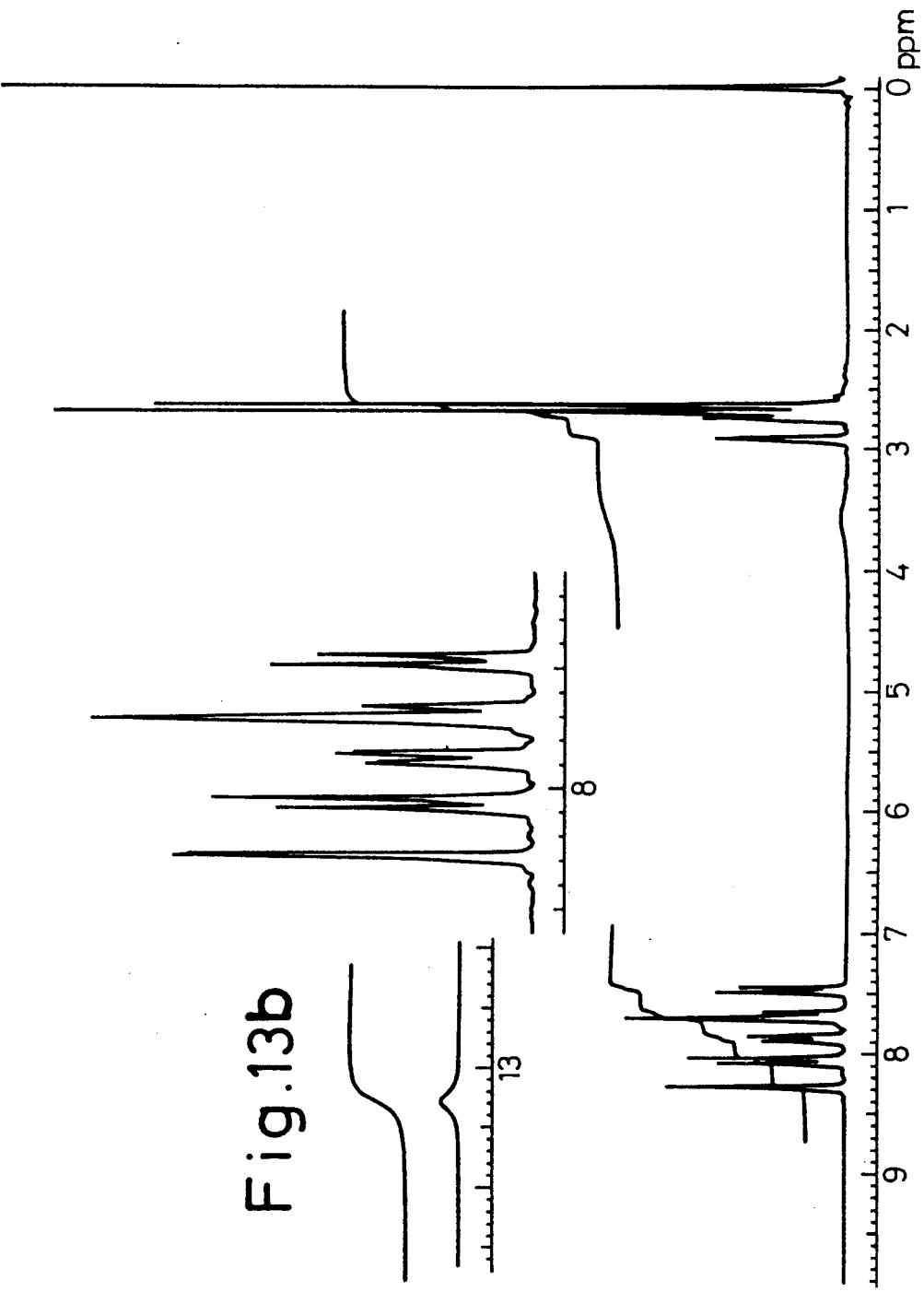

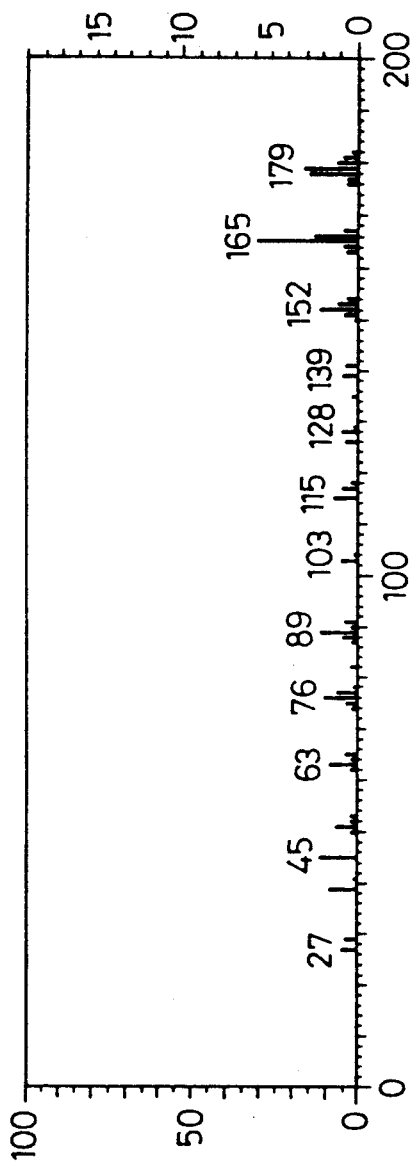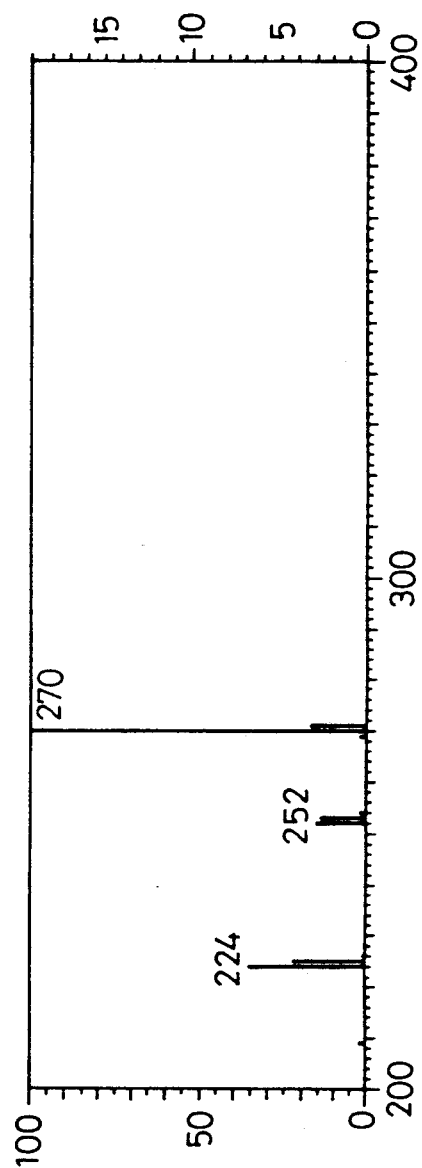

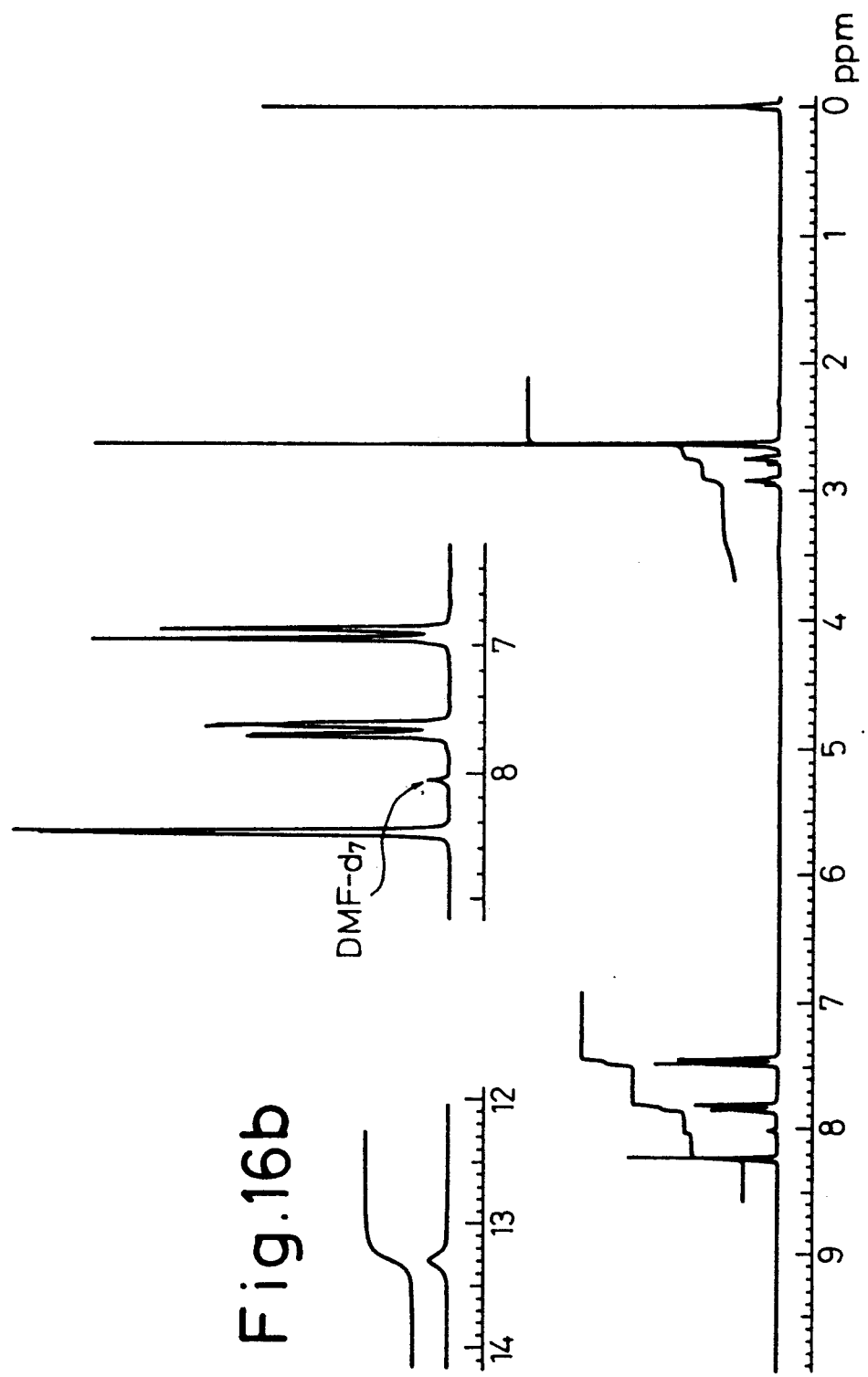

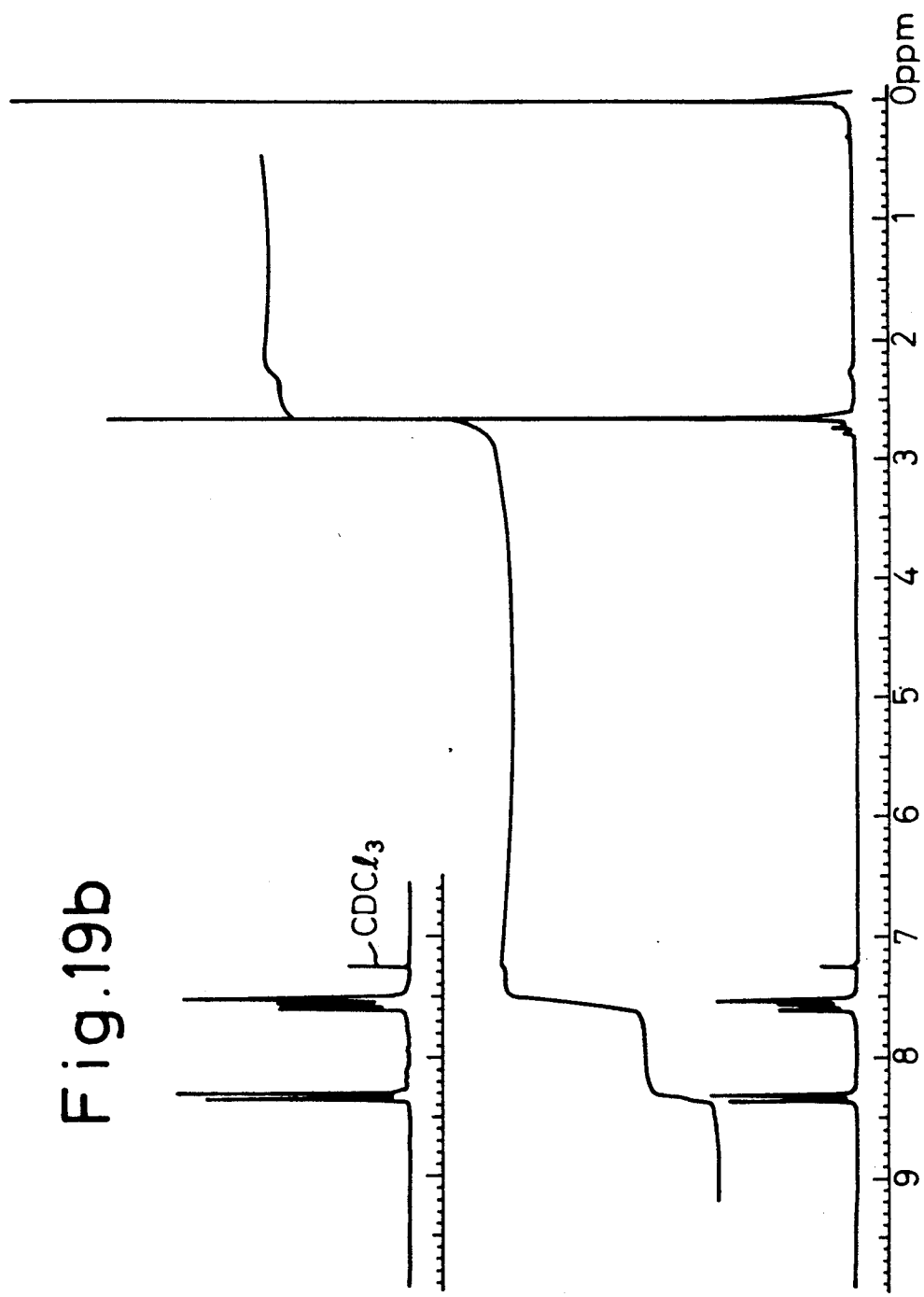

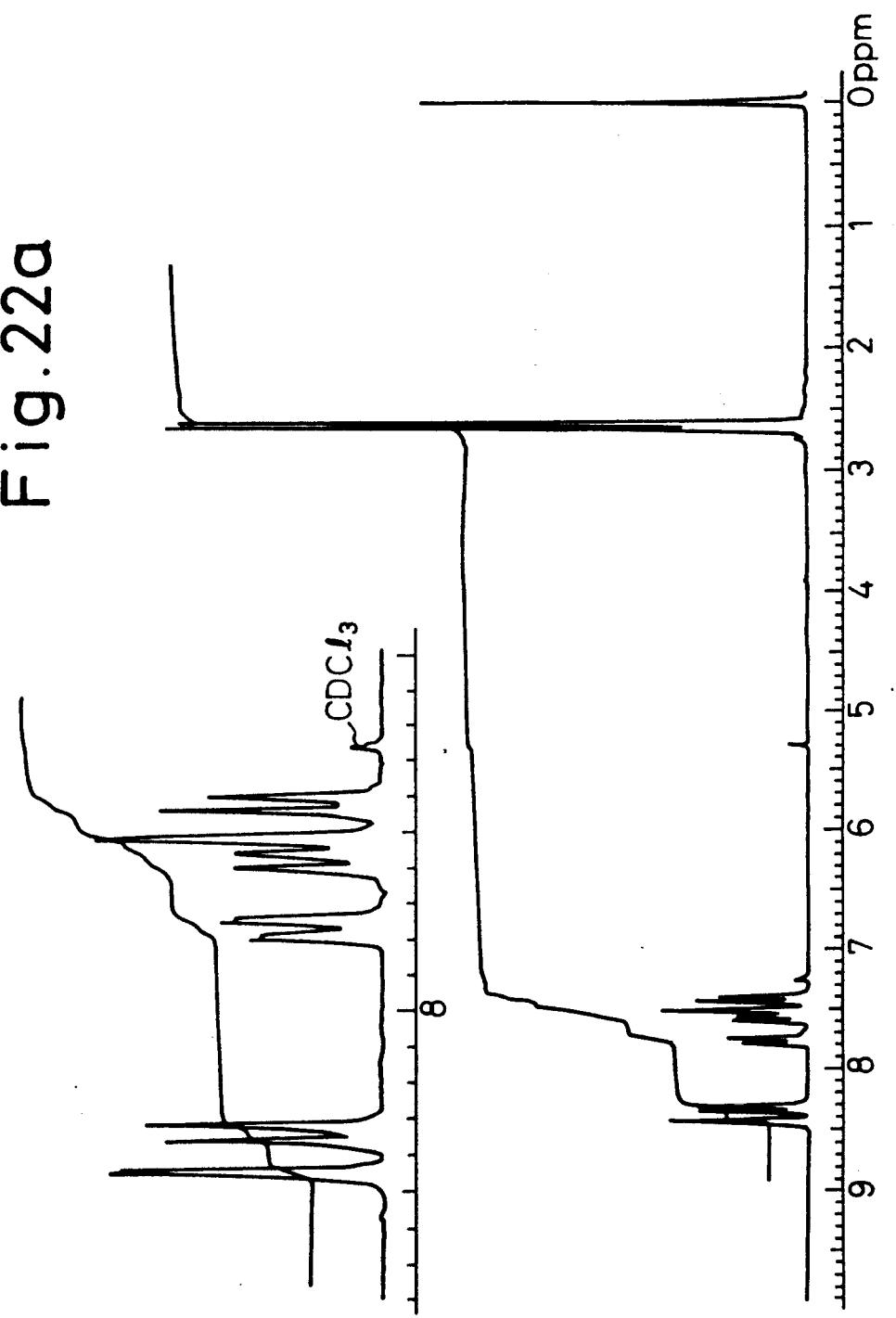

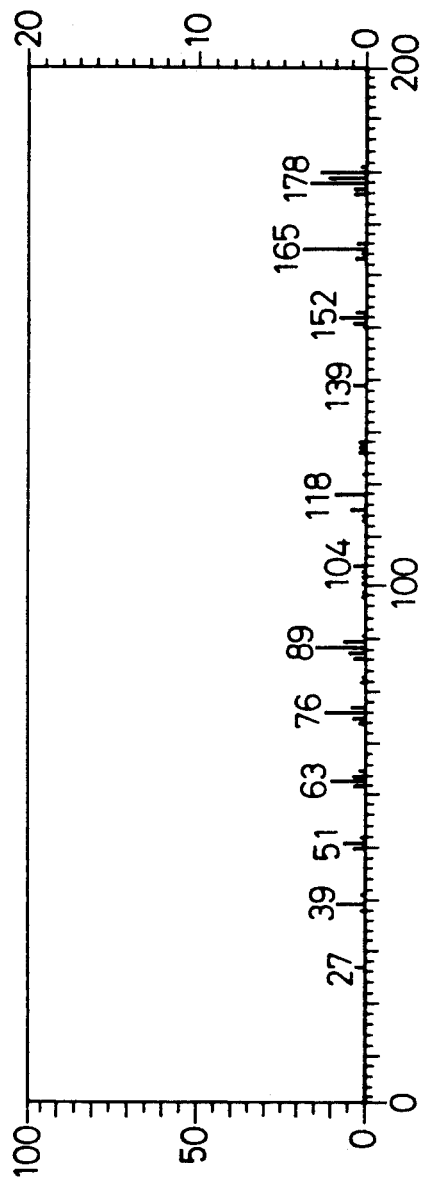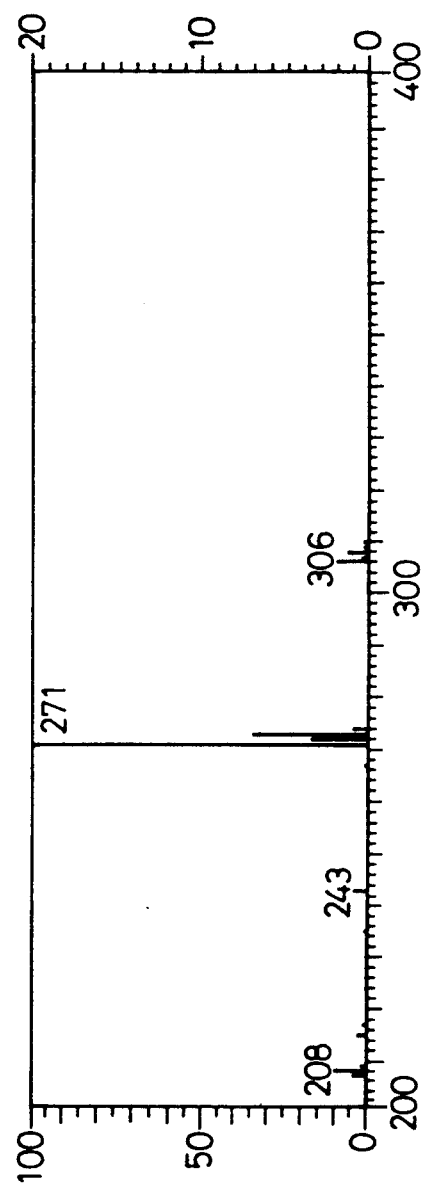

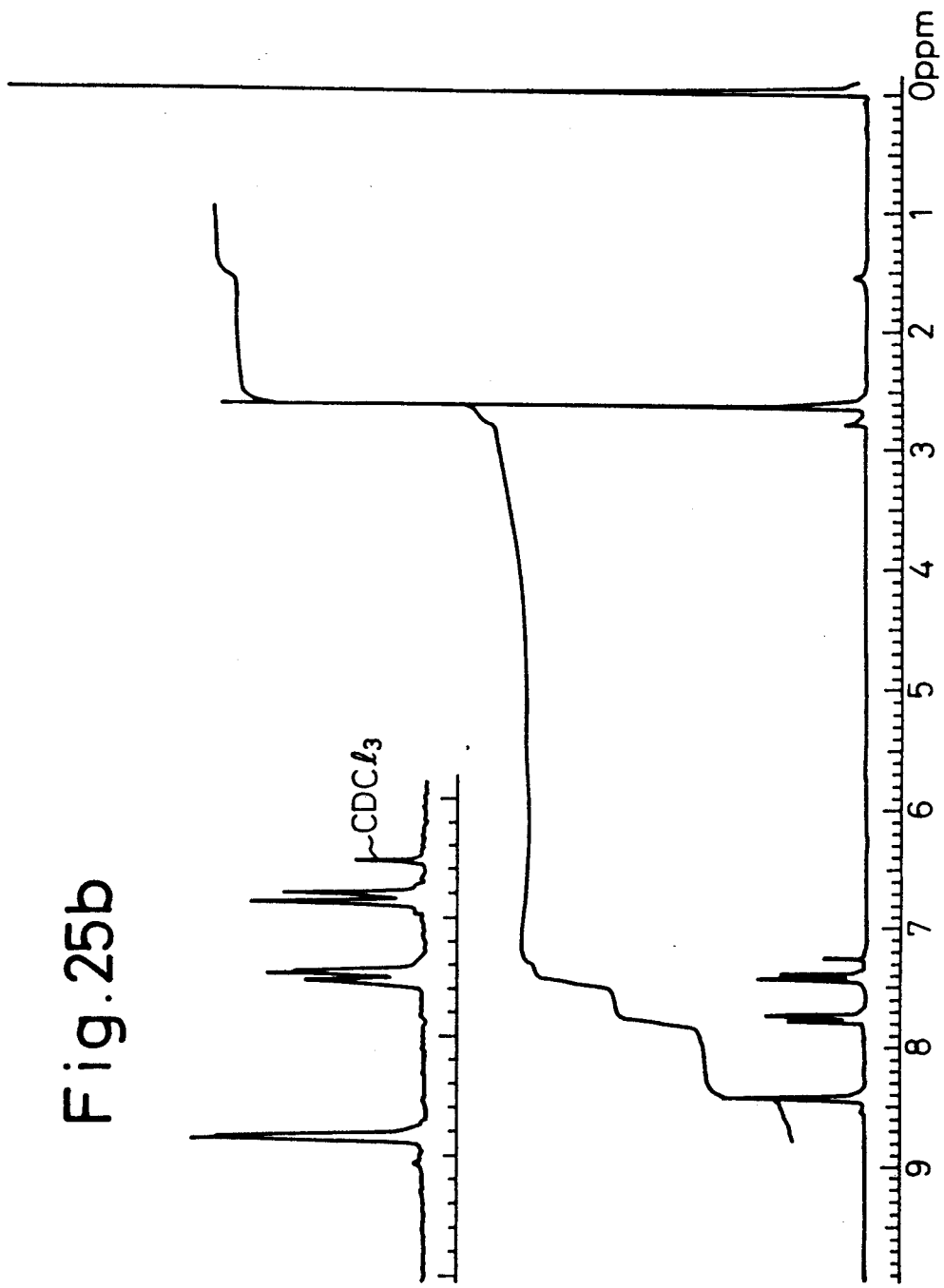

PROCESS OF PRODUCTION OF 3,4,3',4'-SUBSTITUTED BIPHENYL COMPOUND

TECHNICAL FIELD

The present invention relates to a process for the production of a 3,4,3',4'-substituted biphenyl compound. More particularly, the present invention relates to a process for the selective production of a 3,4,3',4'-substituted biphenyl compound from o-toluic acid alkyl esters by an oxidative coupling reaction in the presence of a palladium containing catalyst The 3,4,3',4'-substituted biphenyl compounds produced by the process of the present invention include novel compounds useful for the production of polyesters or polyamides.

BACKGROUND ART

In the past, biphenyl dicarboxylic acid dialkyl esters have been produced by preparing corresponding biphenyl dicarboxylic acids by various known production processes and the esterifying the biphenyl dicarboxylic acids with alcohols.

As the conventional processes for producing the biphenyl carboxylic acids, there are known a process for causing coupling of a 3-bromo benzoic acid by a treatment with a KOH-methanol aqueous solution in the presence of a Pd/C catalyst (U.S. Pat. No. 2,809,210), a process for preparing a Grignard reagent from 4,4'-dichlorobiphenyl, then causing a reaction of the resultant reagent with $CO_2$ (U.S. Pat. No. 2,508,022), a process for oxidizing 3,3'-dimethyl biphenyl by using potassium permanganate (Journal of American Chemistry; J. Am. Chem. Soc. 72, 3221 (1950)), a process for iodizing biphenyl, then causing a reaction of the resultant product with carbon monoxide (Japanese Unexamined Patent Publication No. 63-104942), and a process for oxidizing 4,4'-diisopropyl biphenyl with molecular oxygen (Japanese Unexamined Patent Publication No. 63-122645).

Further, as another process for producing the above-mentioned biphenyl- dicarboxylic acid, there is known the process for oxidizing 3,3',4,4'-tetramethyl biphenyl with molecular oxygen to synthesize 3,3'-dimethyl biphenyl-4,4'-dicarboxylic acid (Japanese Examined Patent Publication (Kokoku) No. 52-3377).

Nevertheless, these conventional processes for producing biphenyl dicarboxylic acid suffer from many defects, e.g., it is difficult to acquire the materials, extremely complicated and long steps are required, and there are many byproducts. Accordingly, all of the conventional processes in which biphenyl dicarboxylic acid is produced and then biphenyl dicarboxylic acid dialkyl esters are produced therefrom, have a poor practically in industrial terms.

Further, it was difficult to selectively manufacture 3,4,3',4'-substituted dimethyl biphenyl dicarboxylic acid dialkyl esters by the conventional processes or by processes provided by combinations of the same.

DISCLOSURE OF THE INVENTION

The object of the present invention is to provide a process for producing 3,4,3',4'-substituted dimethyl biphenyl dicarboxylic acid compounds with a high selectivity. Also, the process of the present invention enables a novel 3,4,3',4'-substituted dimethyl biphenyl dicarboxylic acid compounds to be obtained.

The process of the present invention is a process for producing a 3,4,3',4'-substituted biphenyl compound, comprising the steps of:

oxidatively coupling an o-toluic acid alkyl ester represented by the following general formula (I):

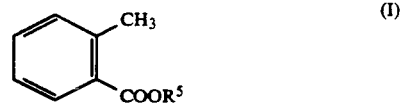
(I)

in which formula (I), $R^5$ represents an alkyl group having 1 to 5 carbon atoms, in the presence of a catalyst containing at least one member selected from the group consisting of mixtures of palladium salts with at least one member selected from 1,10-phenanthroline and α,α'-bipyridine, in an amount of 0.9 to 4 times the molar amount of palladium salts chelating products of palladium salts with 1,10-phenanthroline, and chelating products of palladium salts with α,α'-bipyridine, in an atmosphere containing molecular oxygen, to selectively produce a dimethyl biphenyl dicarboxylic acid dialkyl ester having two methyl groups and two alkoxy carbonyl groups substituted at 3, 4, 3', and 4'-positions of the biphenyl ring structure;

and optionally converting the resultant dimethyl biphenyl dicarboxylic acid dialkyl ester to a corresponding dimethyl biphenyl dicarboxylic acid, and then optionally further converting it to a corresponding dimethyl biphenyl dicarboxylic acid dichloride, to prepare a compound represented by the general formula (II):

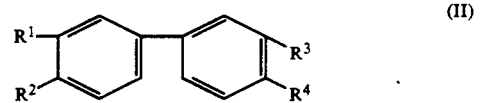
(II)

wherein, one of $R^1$ and $R^2$ represents a —$CH_3$ group and the other one thereof represents a —$COOR^5$ group (wherein $R^5$ is the same as previously defined), a —COOH group, or a —COCl group, and one of $R^3$ and $R^4$ represents a —$CH_3$ group and the other one thereof represents a —$COOR^5$ group (wherein $R^5$ is the same as previously defined), a —COOH group, or a —COCl group.

The 3,4,3',4'-substituted biphenyl compounds produced by the process of the present invention include, as novel compounds, the compounds of the above-mentioned general formula (II) wherein one of $R^1$ and $R^2$ represents a —$CH_3$ group and the other thereof represents a —$COOR^5$ group (wherein $R^5$ is the same as previously defined), a —COOH group, or a —COCl group, and one of $R^3$ and $R^4$ represents a —$CH_3$ group and the other thereof represents a —$COOR^5$ group (wherein $R^5$ is the same as previously defined), a —COOH group, or a —COCl group, $R^1$ and $R^3$ never both being a —$CH_3$ group and $R^2$ and $R^4$ never both being a —$COOR^5$ group, —COOH group, or —COCl group, in other words, the compounds of the formula (II) in which each of $R^1$ and $R^4$ represents a —$CH_3$ group and each of $R^2$ and $R^3$ represents a —$COOR^5$ group (wherein $R^5$ represents an alkyl group having 1 to 5 carbon atoms), a —COOH group, or a —COCl group, and the compounds of the formula (II) in which $R^1$ and $R^3$ represent a —$COOR^5$ group (wherein $R^5$ is the same as previously defined), a —COOH group, or a —COCl group, respectively, and $R^2$ and $R^4$ represent a $—CH_3$ groups, respectively.

BRIEF DESCRIPTION OF THE DRAWINGS

FIG. 1(a) and FIG. 1(b) are $^1H$ NMR analysis charts of a compound of the following formula (Q):

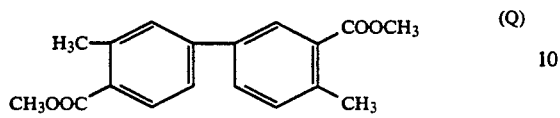

Figure 2A:
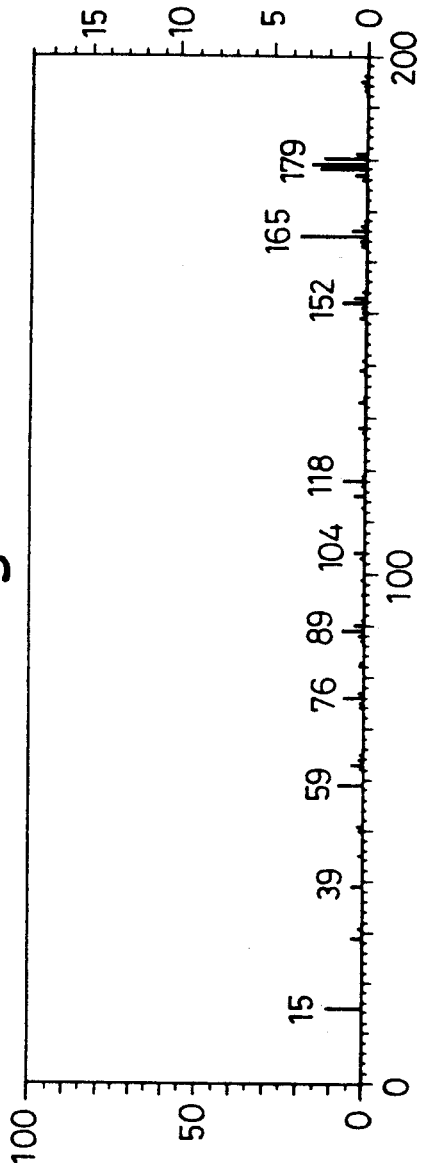
Figure 2B:
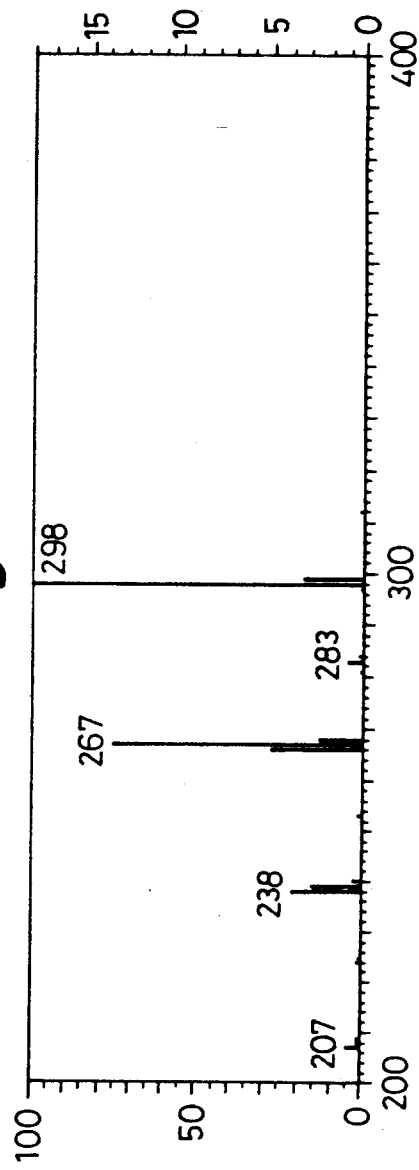
Figure 3:
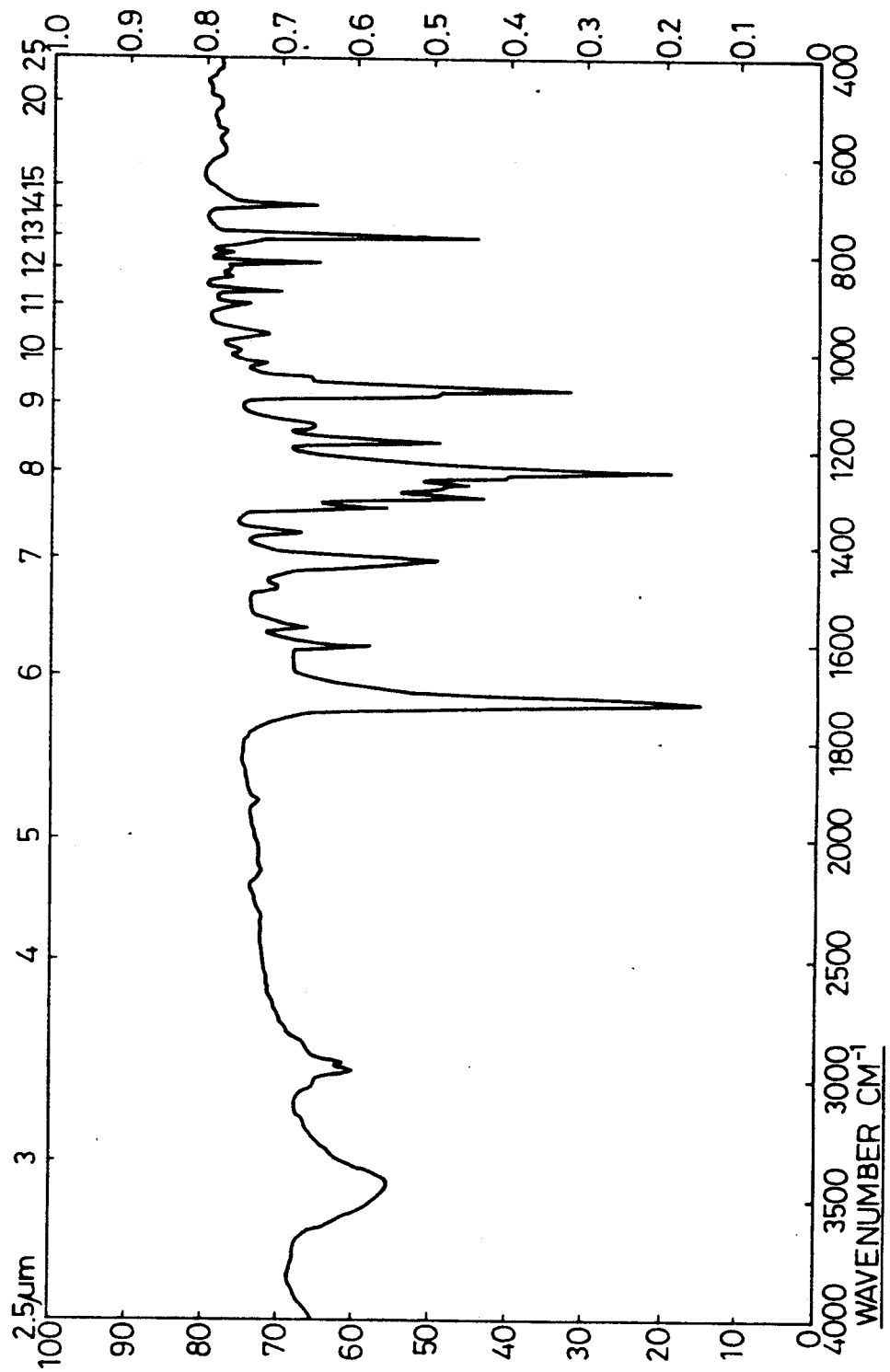

FIG. 2(a) and FIG. 2(b) are mass analysis charts of the compound of the above formula (Q), FIG. 3 is an IR analysis chart of the compound of the above-formula (Q), FIG. 4(a) and FIG. 4(b) are 1H NMR analysis charts of a compound of the following formula (R):

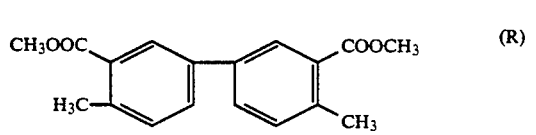

Figure 5A:
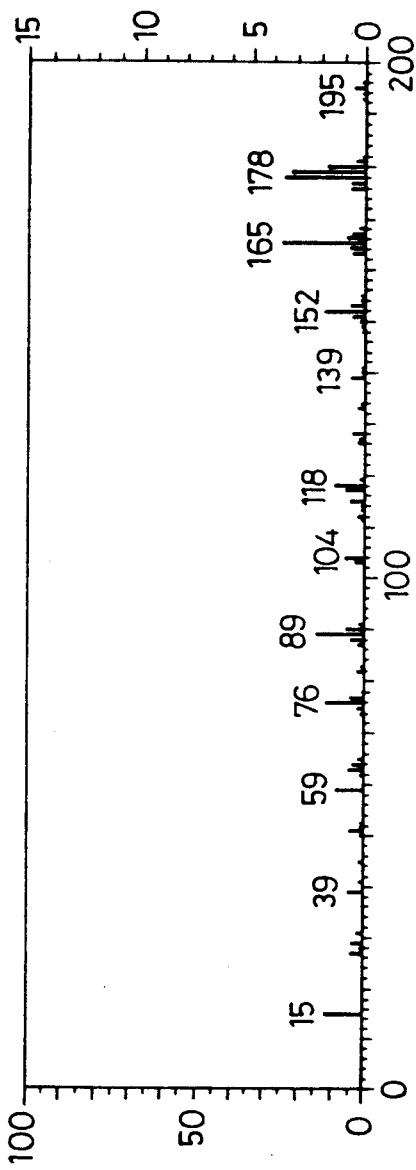
Figure 5B:
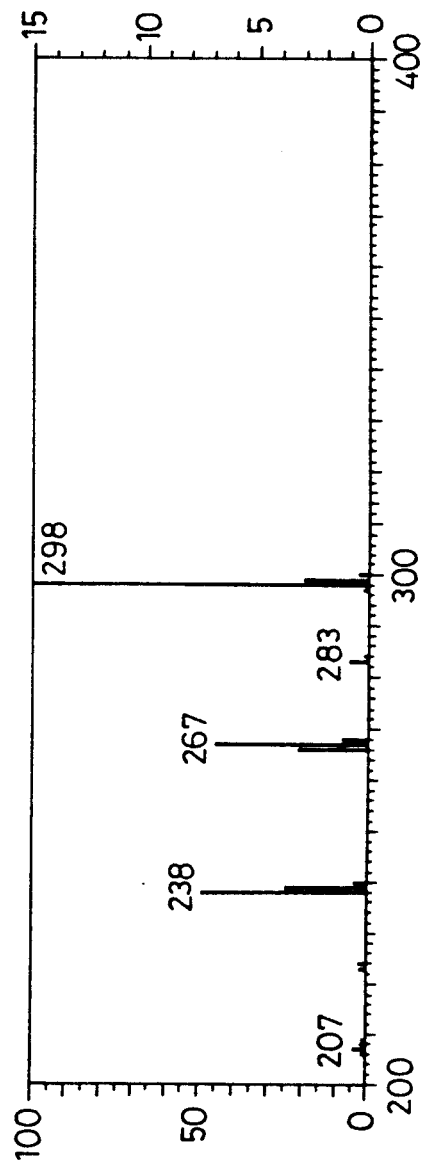

FIG. 5(a) and FIG. 5(b) are mass analysis charts of the compound of the above formula (R), FIG. 6 is an IR analysis chart of the compound of the above formula (R), FIG. 7(a) and FIG. 7(b) are 1H NMR analysis charts of a compound of the following formula (P):

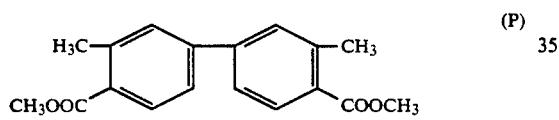

Figure 8A:
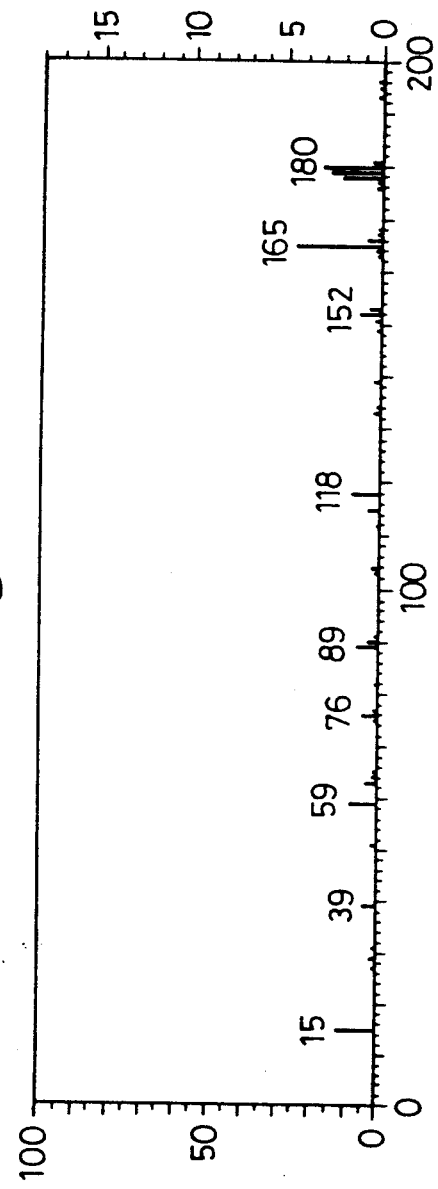
Figure 8B:
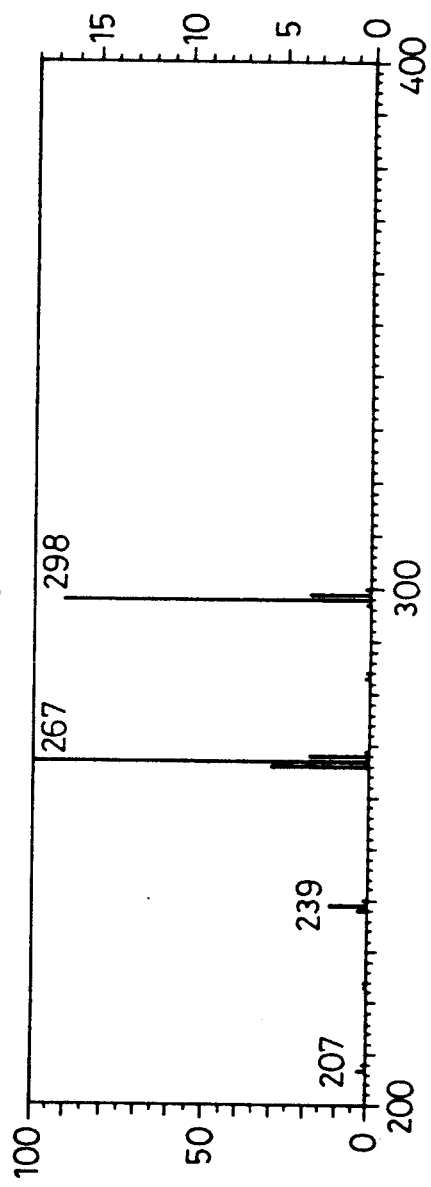
Figure 9:
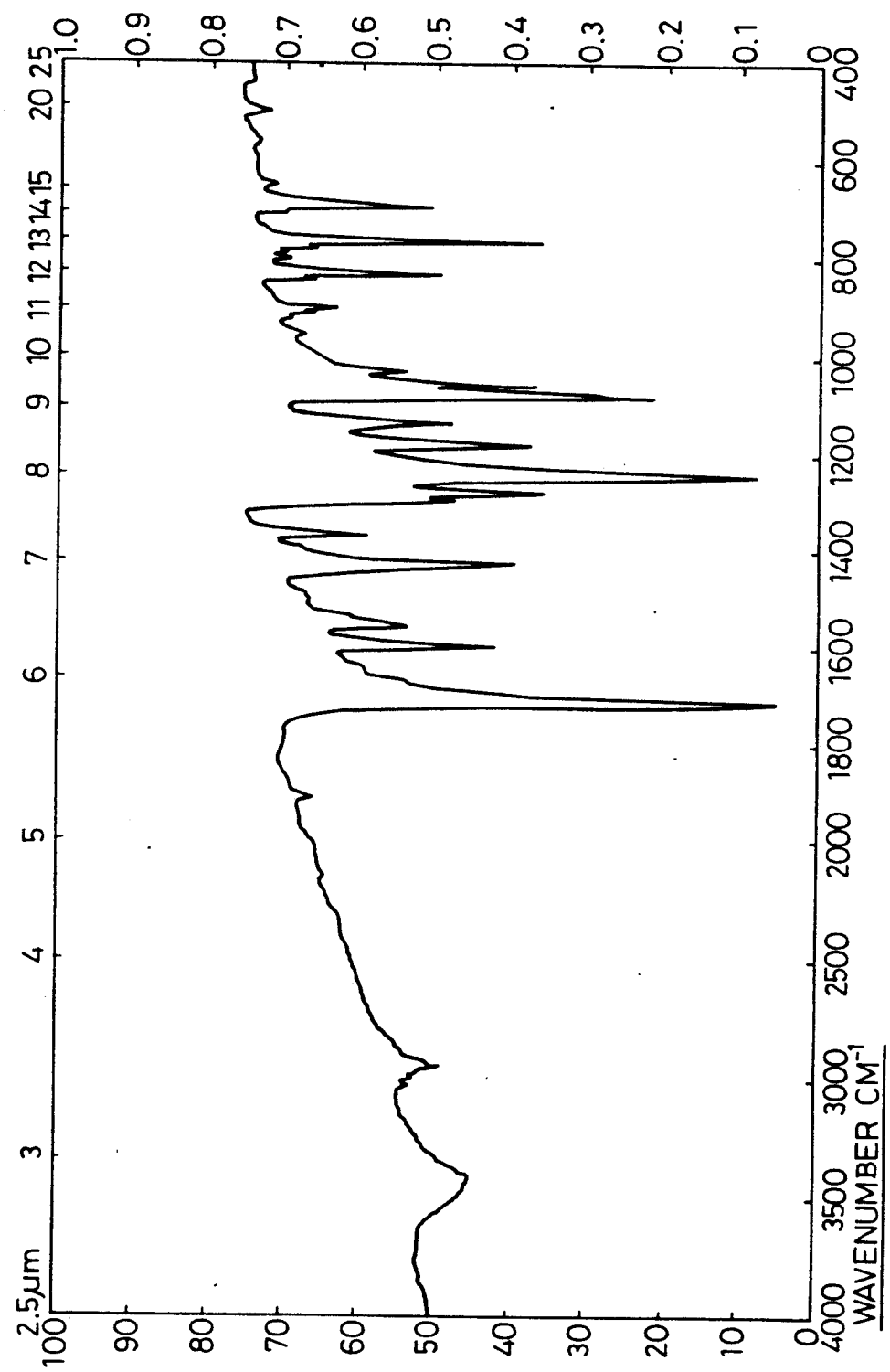

FIG. 8(a) and FIG. 8(b) are mass analysis charts of the compound of the above formula (P), FIG. 9 is an IR analysis chart of the compound of the above formula (P), FIG. 10(a), FIG. 10(b), and FIG. 10(c) are $^1H$ NMR analysis charts of a compound of the following formula (Pa):

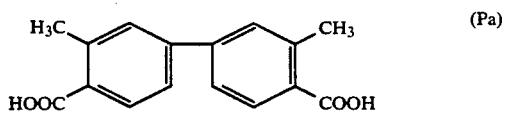

Figure 12:
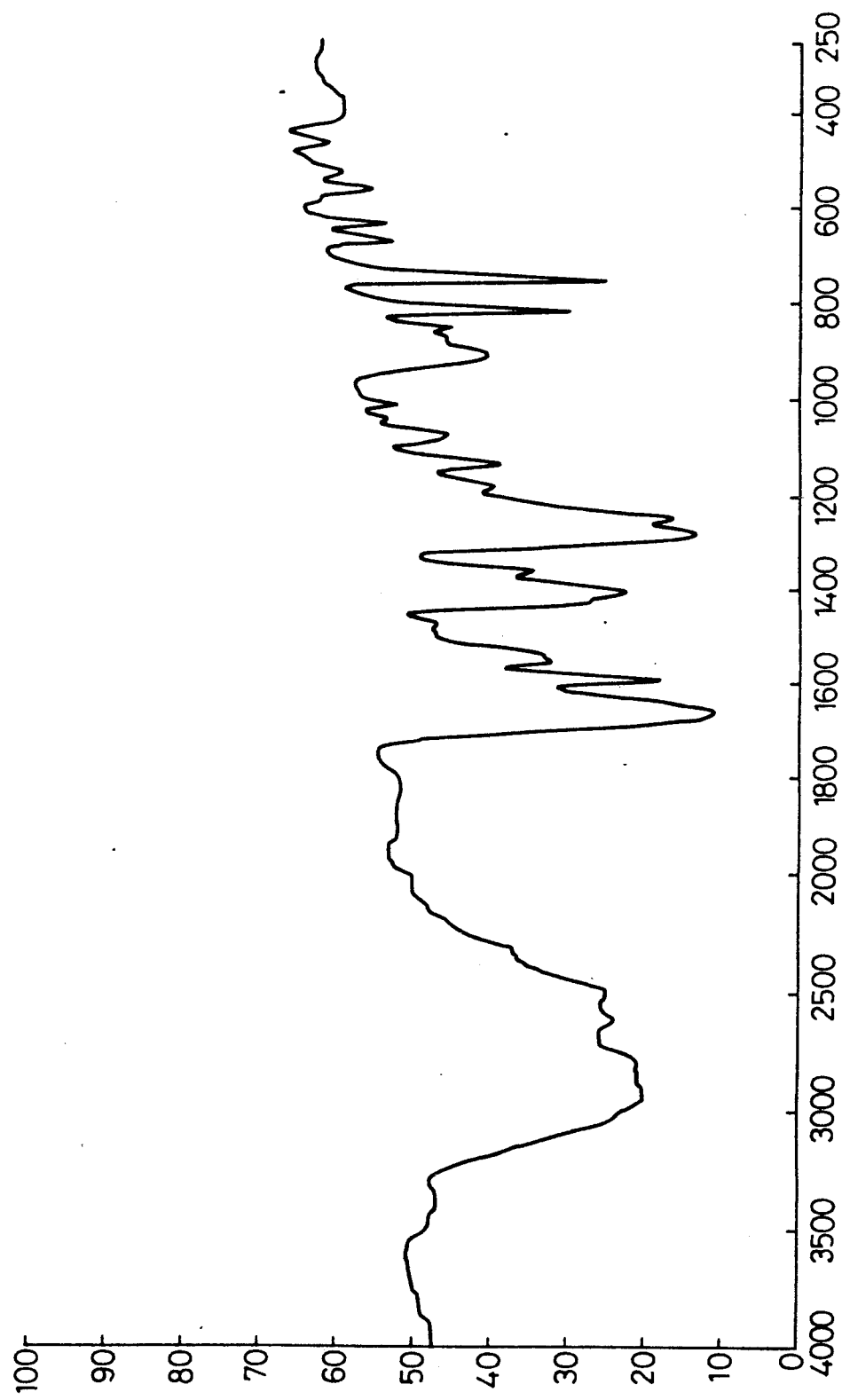

FIG. 11(a) and FIG. 11(b) are mass analysis charts of the compound of the above formula (Pa), FIG. 12 is an IR analysis chart of the compound of the above formula (Pa), FIG. 13(a), FIG. 13(b), FIG. 13(c) are $^1H$ NMR analysis charts of a compound of the following formula (Qa):

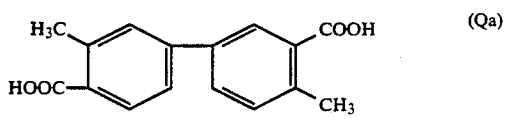

Figure 15:
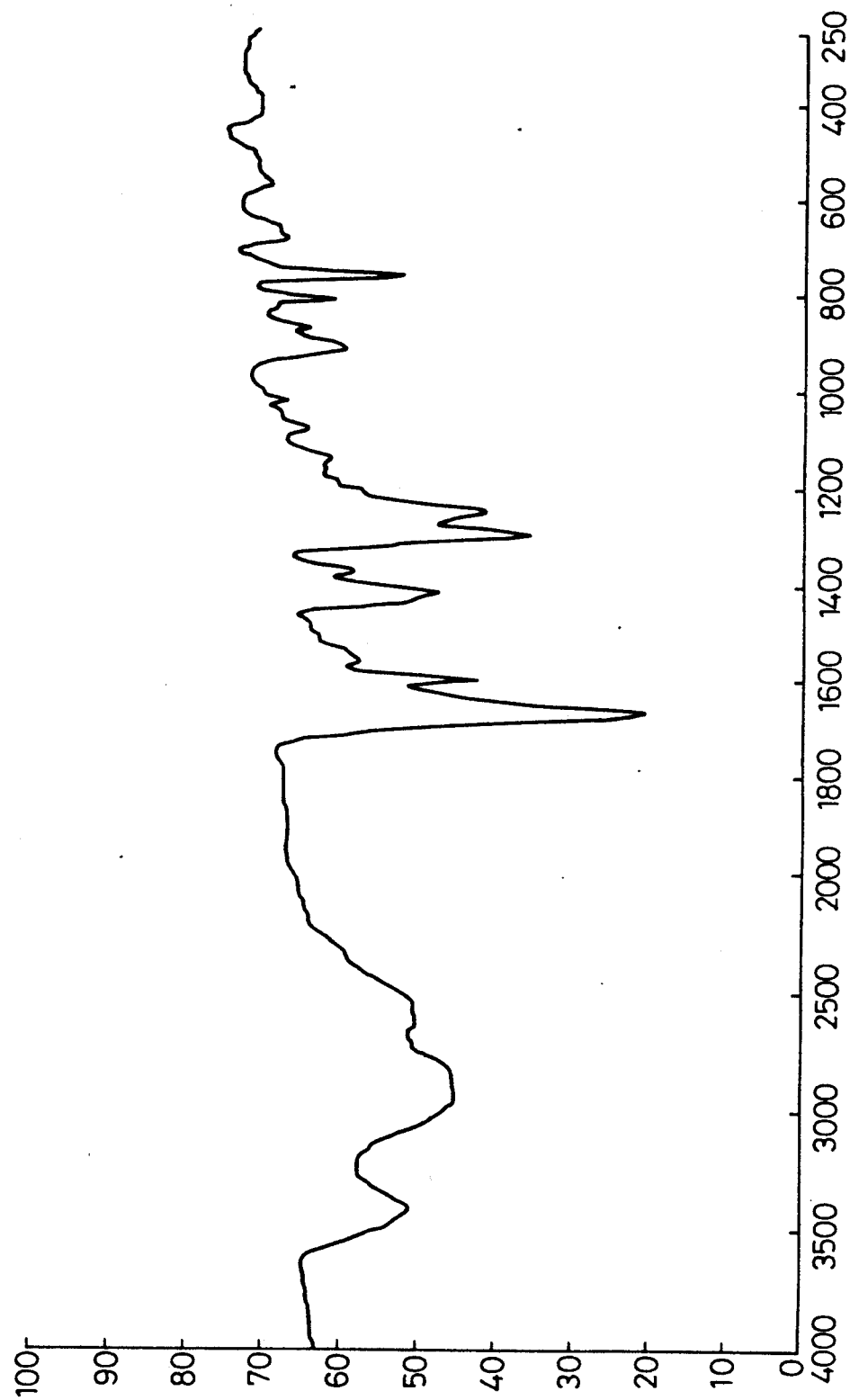

FIG. 14(a) and FIG. 14(b) are mass analysis charts of the compound of the above formula (Qa), FIG. 15 is an IR analysis chart of the compound of the above formula (Qa), FIG. 16(a), FIG. 16(b), and FIG. 16(c) are $^1H$ NMR analysis charts of a compound of the following formula (Ra):

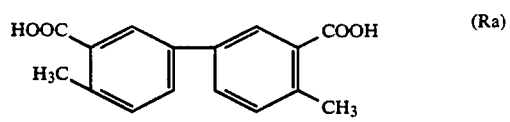

Figure 17A:
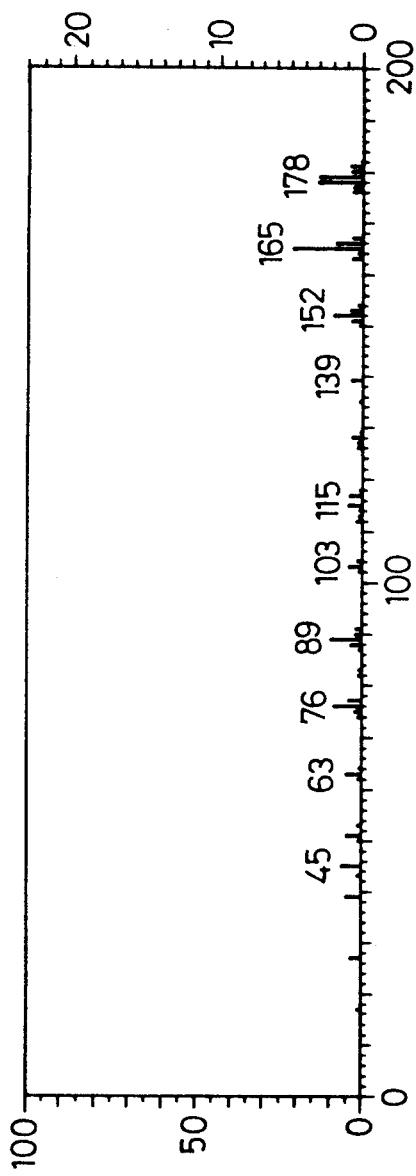
Figure 17B:
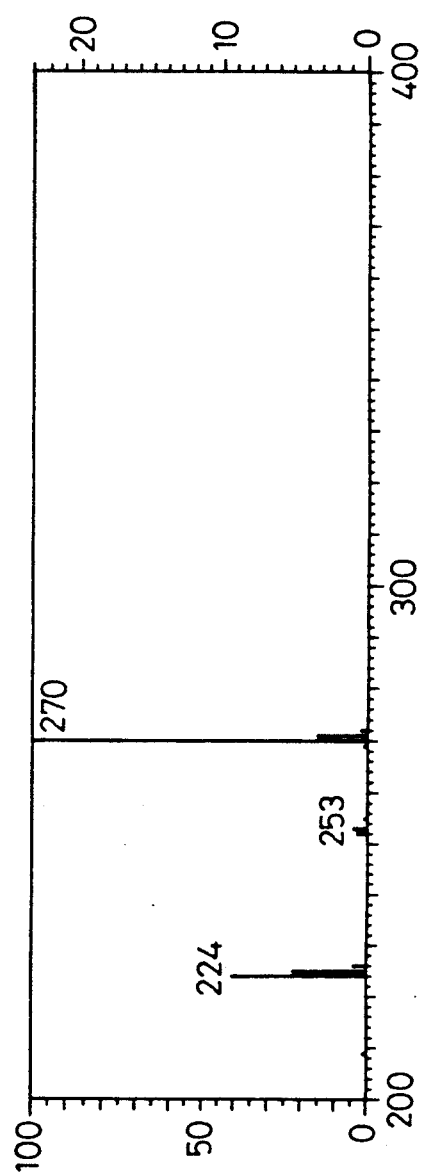
Figure 18:
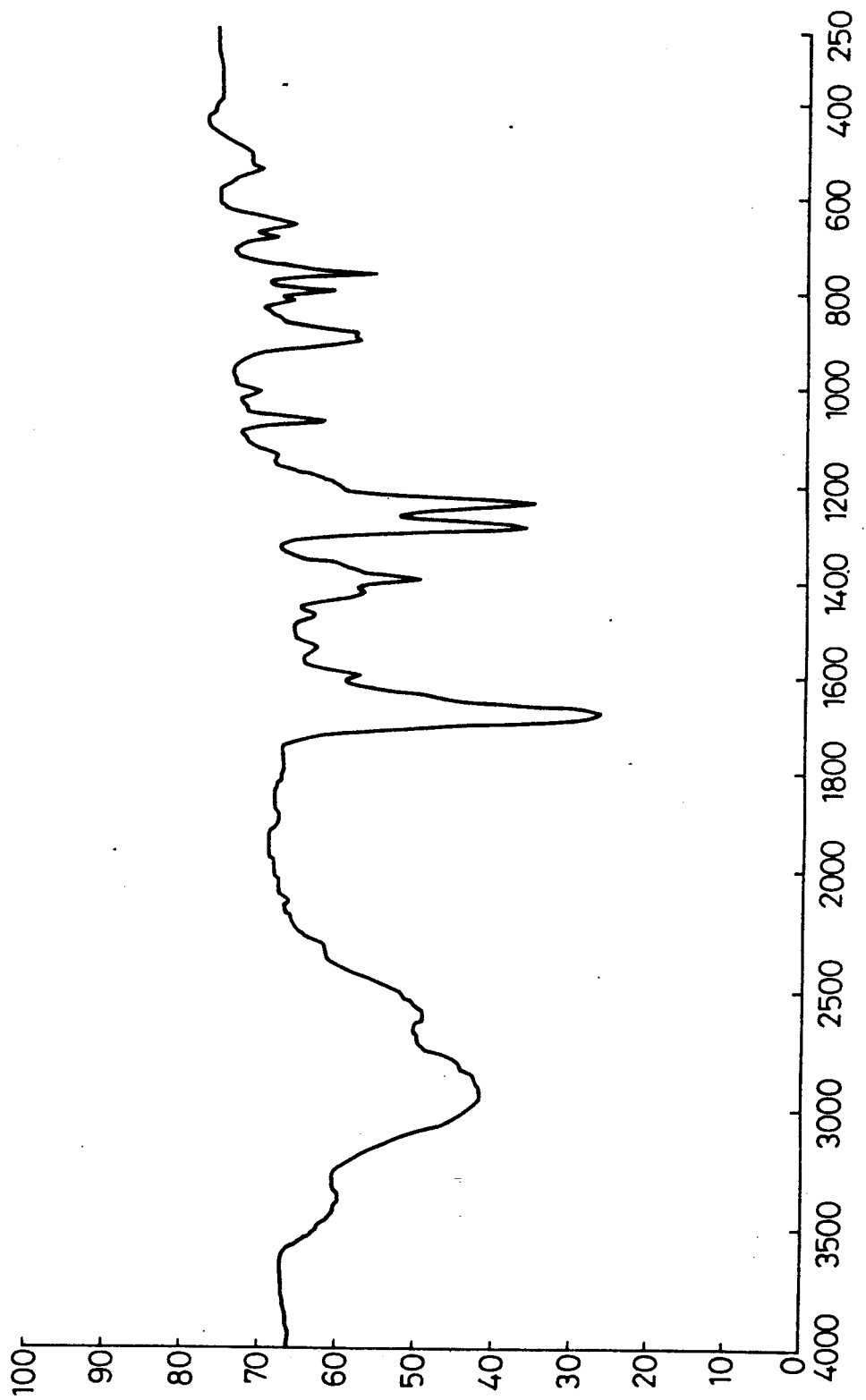

FIG. 17(a) and FIG. 17(b) are mass analysis charts of the compound of the above formula (Ra), FIG. 18 is an IR analysis chart of the compound of the above formula (Ra), FIG. 19(a) and FIG. 19(b) are $^1H$ NMR analysis charts of a compound of the following formula (Pc):

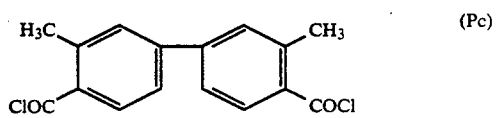

Figure 20A:
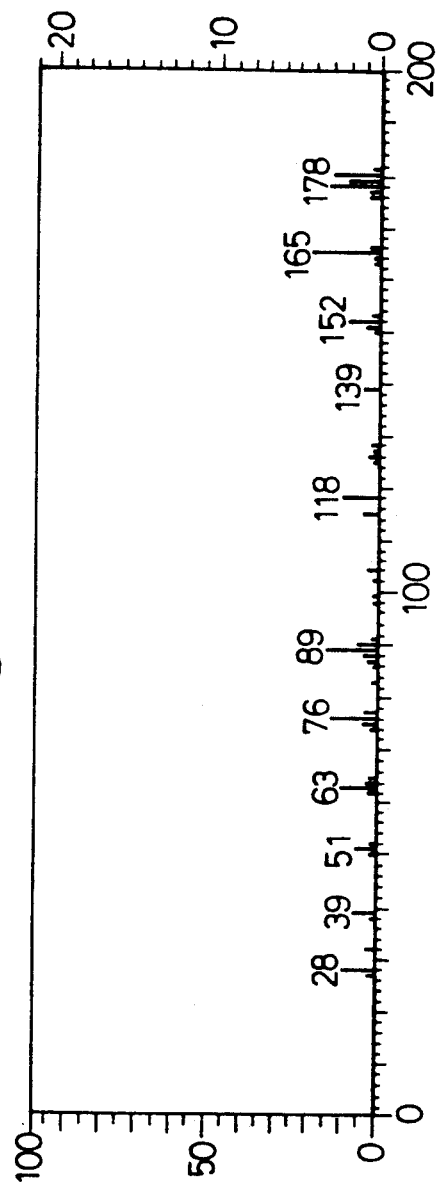
Figure 20B:
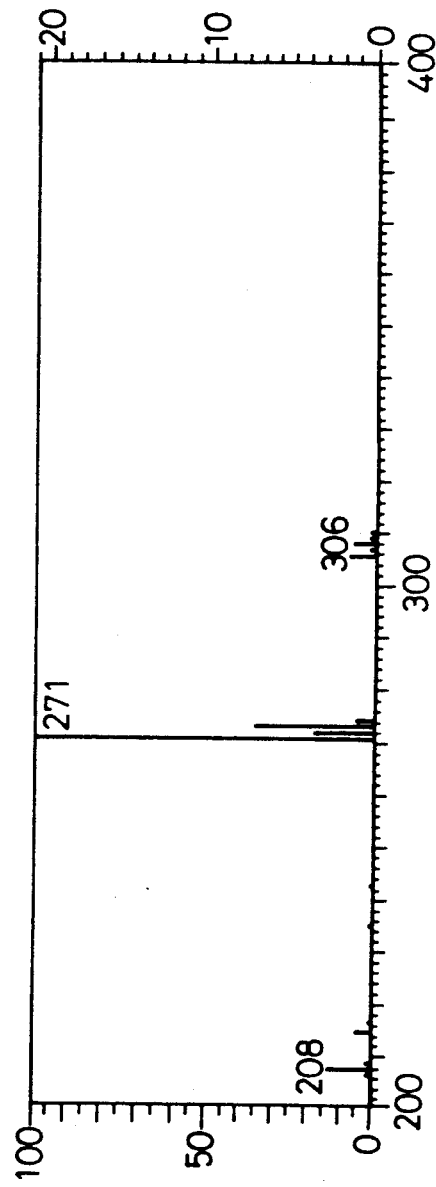
Figure 21:
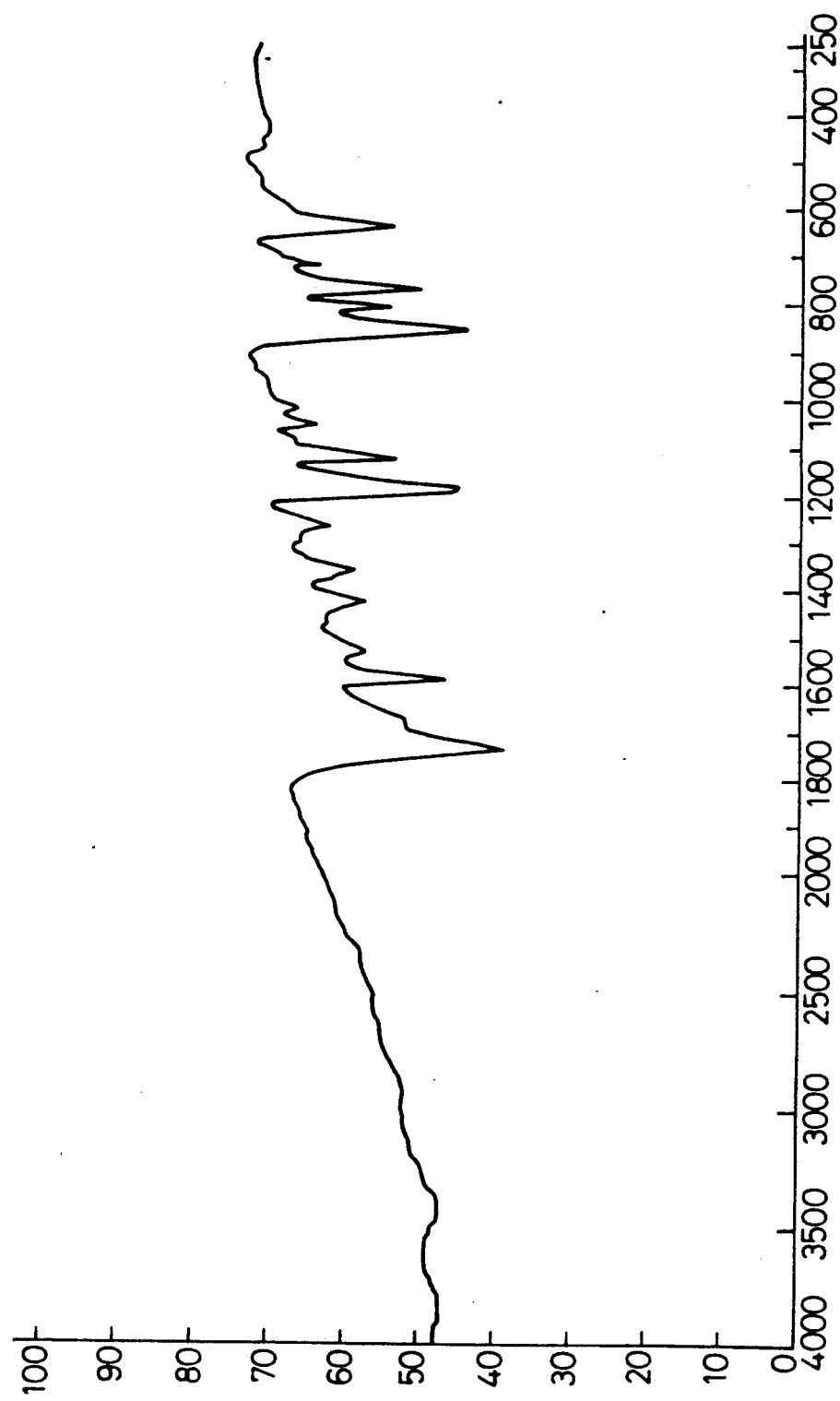

FIG. 20(a) and FIG. 20(b) are mass analysis charts of the compound of the above formula (Pc), FIG. 21 is an IR analysis chart of the compound of the above formula (Pc), FIG. 22(a) and FIG. 22(b) are $^1H$ NMR analysis charts of a compound of the following formula (Qc):

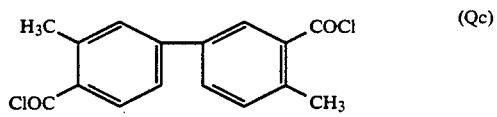

Figure 24:
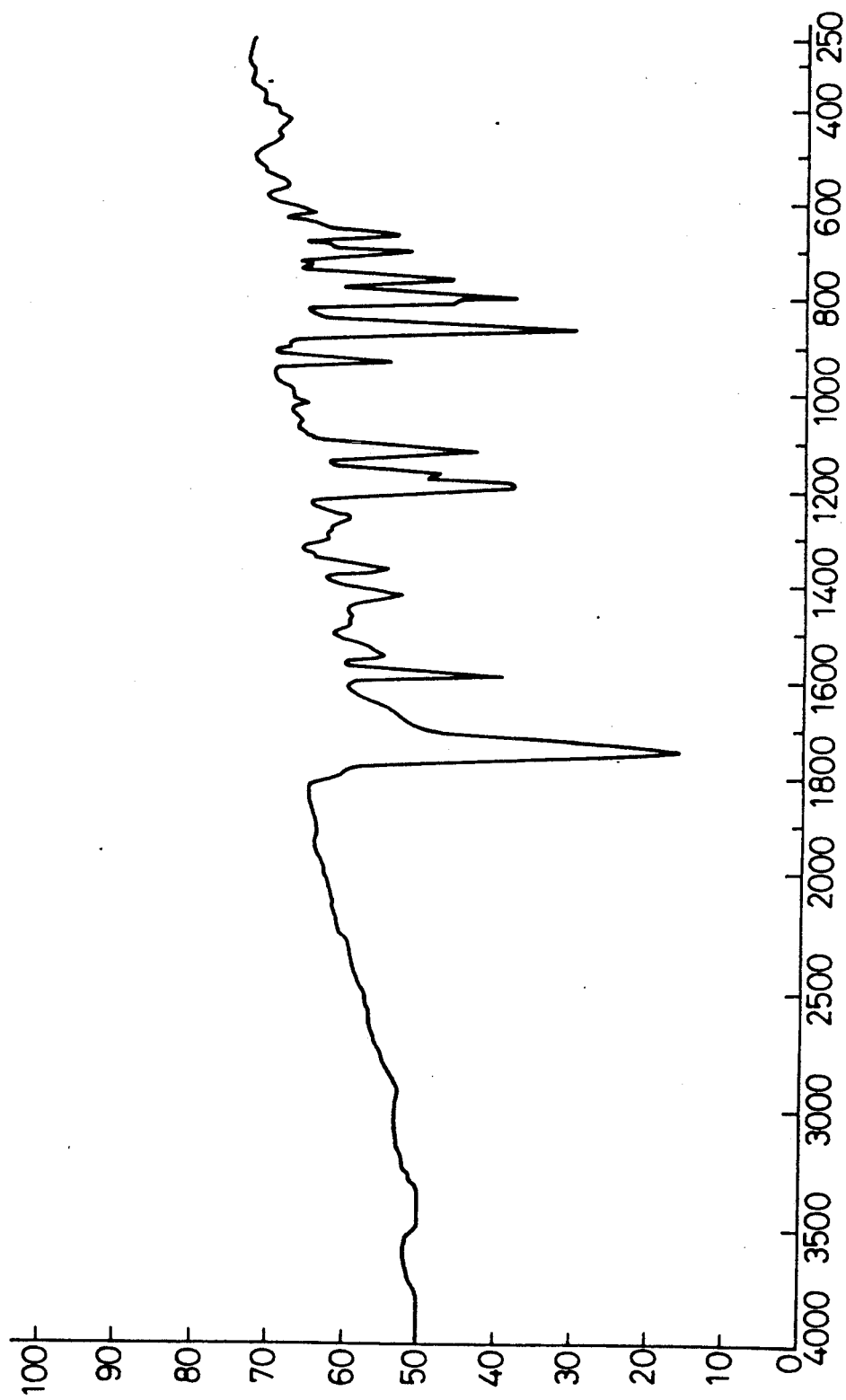

FIG. 23(a) and FIG. 23(b) are mass analysis charts of the compound of the above formula (Qc), FIG. 24 is an IR analysis chart of the compound of the above formula (Qc), FIG. 25(a) and FIG. 25(b) are $^1H$ NMR analysis charts of a compound of the following formula (Rc):

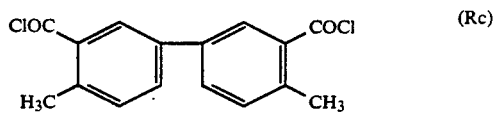

Figure 26A:
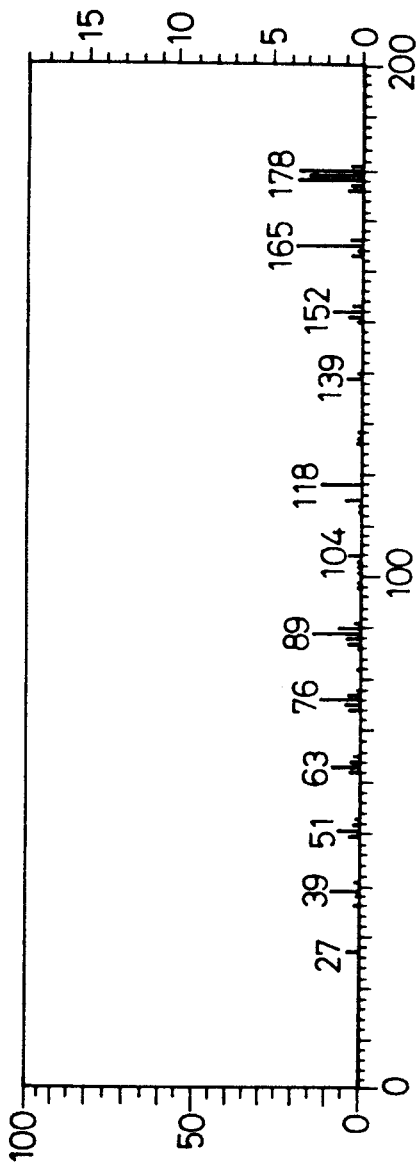
Figure 26B:
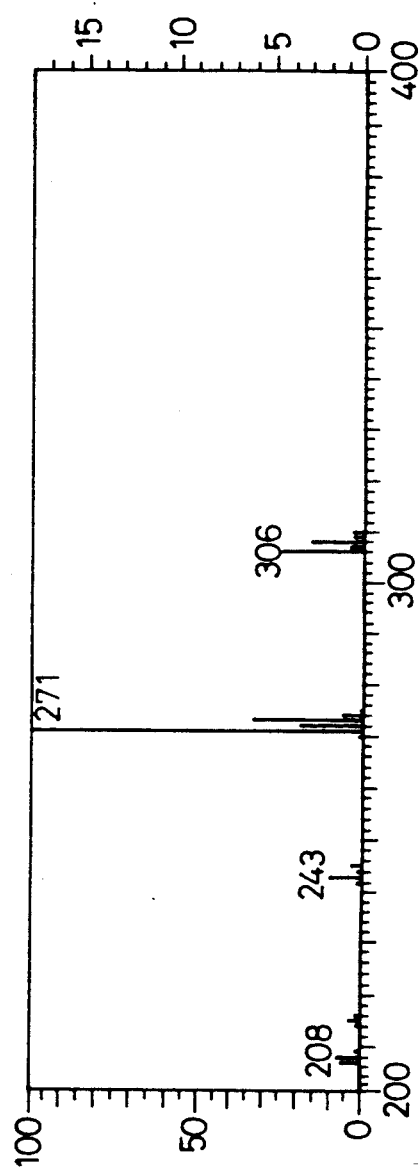
Figure 27:
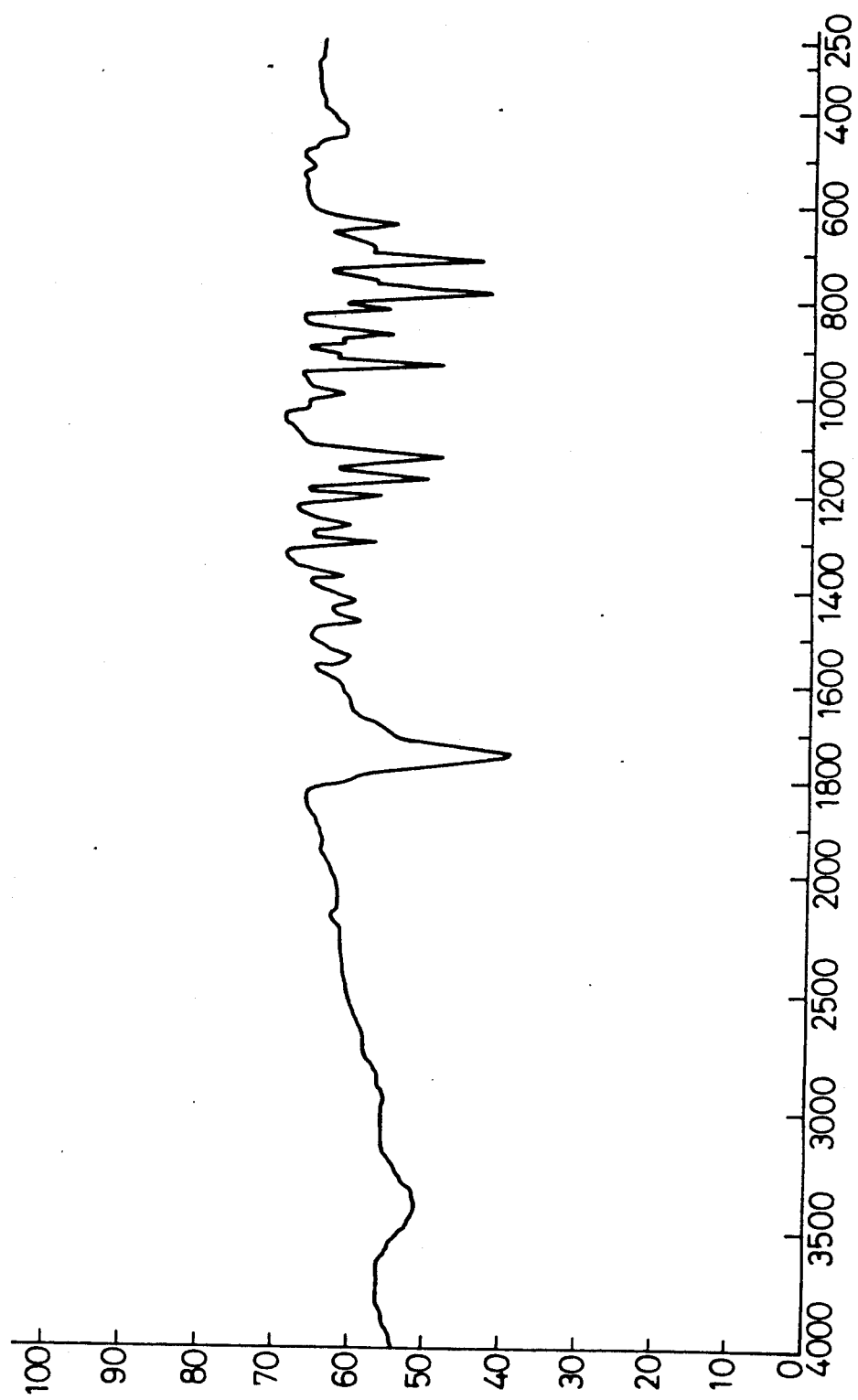

FIG. 26(a) and FIG. 26(b) are mass analysis charts of the compound of the above formula (Rc), and FIG. 27 is an IR analysis chart of the compound of the above formula (Rc).

BEST MODE OF CARRYING OUT THE INVENTION

The dimethyl biphenyl dicarboxylic acid dialkyl esters shown in the above-mentioned general formula (II) includes compounds represented by the following chemical formulae (P), (Q), and (R).

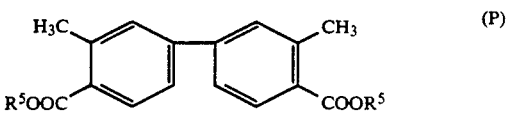

(3,3'-biphenyl-4,4'-dicarboxylic acid dialkyl ester)

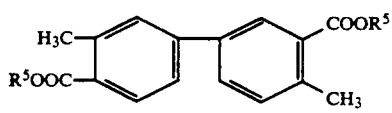

(3,4'-dimethyl-biphenyl-4,3'-dicarboxylic acid dialkyl ester)

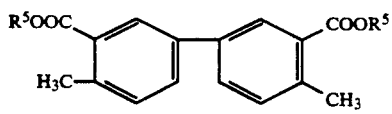

(4,4'-dimethyl-biphenyl-3,3'-dicarboxylic acid dialkyl ester)

In the above-mentioned compounds, the compounds of the formulae (Q) and (R) are novel compounds obtained for the first time by the process of the present invention.

In the process of the present invention, an inexpensive o-toluic acid alkyl ester represented by the formula (I):

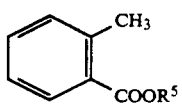

(wherein $R^5$ is the same as previously defined) is used as a starting compound, and this compound is subjected to an oxidative coupling reaction in the presence of a specific palladium-containing catalyst in an atmosphere containing molecular oxygen.

In the above-mentioned oxidative coupling reaction of the process of the present invention the o-toluic acid alkyl ester is oxidatively coupled to form a dimethyl biphenyl dicarboxylic acid alkyl ester having two methyl groups (—$CH_3$) and two carboxylic acid alkyl ester groups (—$COOR^5$) substituted at the 3,4,3',4'-positions thereof.

The above-mentioned o-toluic acid alkyl ester can be produced by an esterification reaction of o-toluic acid with a lower alcohol having 1 to 5 carbon atoms in the presence of a catalyst, for example, sulfuric acid or the like. In the process of the present invention, it is desirable to use o-toluic acid methyl ester or o-toluic acid ethyl ester.

The catalyst usable for the oxidative coupling reaction of the above-mentioned o-toluic acid alkyl ester comprises at least one member selected from the group consisting of;

(a) mixtures of palladium salts with at least one member selected from 1,10-phenanthroline and α,α'-bipyridine in an amount of 0.9 to 4 times the molar amount of palladium salts, (b) chelating products of palladium salts with 1,10-phenanthroline and chelating products of palladium salts with α,α'-bipyridine.

As the above-mentioned palladium salts, palladium salts of organic acids or inorganic acids or palladium chelate salts of β-diketone compounds are usable.

As the above-mentioned organic palladium salts, palladium salts of aliphatic carboxylic acids having 1 to 5 carbon atoms, for example, formic acid, acetic acid, propionic acid, butyric acid and valeric acid, are usable.

As the above-mentioned palladium chelate salts of β-diketone compounds, palladium chelate salts of acetyl acetone, benzoyl acetone, and trifluoroacetyl acetone, are usable.

As the above-mentioned inorganic palladium salts, palladium salts of in organic salts, for example, hydrochloric acid, nitric acid, nitrous acid, sulfuric acid, sulfurous acid and phosphoric acid, are usable. In particular, a palladium salt of nitric acid is preferable.

In the process of the present invention, as a palladium salt, an organic palladium salt, for example, a palladium salt of acetic acid ($Pd(OAc)_2$), is preferably used.

As a component of the catalyst usable for the process of the present invention, a basic bidentate ligand compound selected from 1,10-phenanthroline and α,α'-biphenyl, is used in addition to palladium salts, when 1,10-phenanthroline is used, the resultant palladium-containing catalyst has a superior heat resistance.

In the process of the present invention, it is preferable to use, as a catalyst component, a copper salt along with the above-mentioned palladium-containing component.

As the above-mentioned copper salt, copper salts of aliphatic carboxylic acids having 1 to 5 carbon atoms, for example, formic acid, acetic acid, propionic acid, butyric acid, valeric acid, etc. or copper salts of inorganic acids, for example, hydrochloric acid, nitric acid, nitrous acid, sulfuric acid, sulfurous acid, and phosphoric acid and, further, copper chelated salts of β-diketone compounds, for example, acetyl acetone, benzoyl acetone, and trifluoroacetyl acetone, are usable.

Further, in the process of the present invention, when copper salts is employed, as a catalyst, together with the palladium salts and above-mentioned basic bidentate ligand compound, the above-mentioned three components can be used in the state of a mixture thereof or a mixture of a chelate compound of the palladium and above-mentioned basic bidentate ligand compound with a copper salt (which may be a copper chelated salt).

In the process of the present invention, the amount of the catalyst component consisting of the basic bidentate ligand compound selected from 1,10-phenanthroline and α,α'-bipyridine to be mixed with the palladium salts is 0.9 to 4 moles, preferably 0.95 to 3 moles, per mole of the palladium salts.

Further, in the process of the present invention, the amount of catalyst to be used, is preferably 0.0001 to 0.1 mole, more particularly preferably 0.001 to 0.01 mole, in terms of palladium salt, per mole of o-toluic acid alkyl ester. Further, when a copper salt is used, the amount of copper salt is preferably 0.01 to 10 moles, more preferably 0.02 to 5 moles, per mole of palladium salts.

In the process of the present invention, the reaction temperature of the oxidative coupling reaction is preferably 50° to 300° C., most preferably 60° to 250° C., and the reaction pressure is preferably the ambient atmospheric pressure to 300 atmospheres (atm), most preferably the ambient atmospheric pressure to 100 atmospheres. Further, the oxygen partial pressure in the oxygen-containing atmosphere is preferably 0.05 to 10 atmospheres, most preferably 0.07 to 5 atmospheres. When the oxygen partial pressure is too low in the oxidative coupling reaction of the process of the present invention, for example, when it is 5 atmospheres or less, it is preferable to concurrently use a copper salt in the catalyst.

In the oxidative coupling reaction in the process of the present invention, the air or other molecular oxygen-containing gas can be supplied by the batch system.

Alternatively, the air or other molecular oxygen-containing gas can be continuously circulated through the reaction system (reaction liquid) by bubbling etc.

The oxidative coupling reaction product obtained by the process of the present invention comprises, as a principal product a mixture of the compounds of the above-mentioned formulae (P), (Q), and (R), and these compounds can be isolated, recovered, and purified by a usual distillation method, recrystallization method, etc.

In the process of the present invention, the selectivity of the above-mentioned 3,4,3',4'-substituted dimethyl biphenyl dicarboxylic acid alkyl esters (which refers to a ratio (molar %) of the "total amount of the resultant 3,4,3',4'-substituted derivatives" to the "total amount of the dimer products produced from the toluic acid alkyl esters"), is at least 80 molar %, particularly at least 90 molar %. In general, the dimethyl biphenyl dicarboxylic acid dialkyl esters obtained by dimerization of toluic acid alkyl esters include 10 types of isomers. The process of the present invention has an advantage of enabling a selective production of the 3,4,3',4'-substituted compound with an extremely high selectivity as mentioned above.

Further, in the process of the present invention, the yield of the resultant 3,4,3',4'-substituted dimethyl biphenyl dicarboxylic acid dialkyl ester, based on the molar amount of the palladium salts used as the catalyst component is extremely high, at least 500 mol %, in particular at least 1000 mol %. In other words, in the process of the present invention, the reaction efficiency of the catalyst in the oxidative coupling reaction is extremely high.

The 3,4,3',4'-substituted dimethyl biphenyl dicarboxylic acid dialkyl ester produced by the process of the present invention is useful as the starting material for various types of resin materials.

In the process of the present invention, if necessary, the 3,4,3',4'-substituted dimethyl biphenyl dicarboxylic acid dialkyl ester obtained by the abovementioned oxidative coupling reaction can be converted to the corresponding 3,4,3',4'-substituted dimethyl biphenyl dicarboxylic acid, by a hydrolysis under high temperature and high pressure conditions of, for example, at a temperature of about 150 to 300° C. under a pressure of about 2 to 100 atmospheres or by a hydrolysis with an acid (for example, acetic acid or other aliphatic carboxylic acid) or an alkali (or alkali salt).

The compounds obtained by the above-mentioned hydrolysis include the compounds of the formulae (Pa), (Qa), and (Ra):

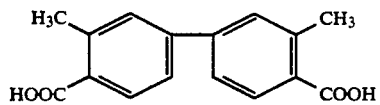

(3,3'-dimethyl-diphenyl-4,4'-dicarboxylic acid)

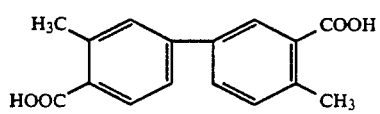

(3,4'-dimethyl-biphenyl-4,3'-dicarboxylic acid)

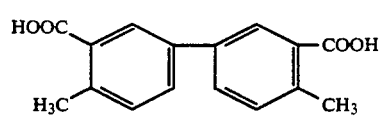

(4,4'-dimethyl-biphenyl-3,3'-dicarboxylic acid)

Among the above-mentioned compounds, the compounds of the formulae (Qa) and (Ra) are novel compounds obtained for the first time by the process of the present invention.

In the above-mentioned hydrolysis using an alkali or alkali salt, above, it is preferable to use caustic alkali, for example, caustic soda or caustic potash, or salts of the above-mentioned alkali. The amount of these caustic alkali to be used is preferably two to three times the molar amount of the dimethyl biphenyl dicarboxylic acid dialkyl esters.

In the above-mentioned alkali hydrolysis, the reaction time can be shortened by adding a lower alcohol, for example, n-butanol or propanol to the reaction system, and this is preferable.

By adding an acid, for example, hydrochloric acid or sulfuric acid to the above-mentioned hydrolysis reaction system to make it acidic the target product, i.e., the dimethyl biphenyl dicarboxylic acid is precipitated, and can be isolated.

The above-mentioned dimethyl biphenyl dicarboxylic acid is usable, as a monomer component for producing polyesters or polyamides by polymerizing with diols or diamines.

Further, the novel compounds of formulae (Qa) and (Ra) are useful for the production of various polymers having superior moldability.

In the process of the present invention, if necessary, the above-mentioned dimethyl biphenyl dicarboxylic acids can be converted to corresponding dimethyl biphenyl dicarboxylic acid dichlorides by applying thereto a chloridization treatment.

The above-mentioned dichloride compounds include the compounds of the following formulae (Pc), (Qc), and (Rc):

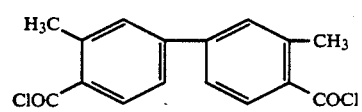

(3,3'-dimethyl-biphenyl-4,4'-dicarboxylic acid dichloride)

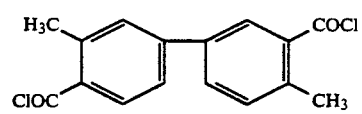

(3,4'-dimethyl-biphenyl-4,3'-dicarboxylic acid dichloride)

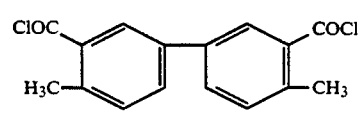

(4,4'-dimethyl-diphenyl-3,3'-dicarboxylic acid dichloride)

In the above-mentioned compounds, the compounds of the formulae (Qc) and (Rc) are novel compounds obtained for the first time by the process of the present invention.

The above-mentioned chloridization is effected by adding a chloridization agent including at least one member selected from phosphorus trichloride, phosphorus pentachloride, and thionyl chloride to an aqueous solution of dimethyl biphenyl dicarboxylic acid, and heating the resultant reaction mixture at a temperature of, for example, from room temperature to 200° C. An chloridization agent containing thionyl chloride is preferably employed.

Also, for the chloridization, pyridine, dimethyl formamide, or the like may be add, as a catalyst to the reaction mixture. In general, such a chloridization reaction catalyst is used in an amount of 0.5 mole to 2.0 moles, per mole of the chloridization agent.

The 3,4,3',4'-substituted dimethyl biphenyl dicarboxylic acid dichloride produced by the process of the present invention is useful as a starting material for various resin materials.

EXAMPLES

The present invention will be further explained by the following examples.

Example 1

Oxidative Coupling Reaction

A reflux condenser, thermometer, agitator, and gas blowing pipe were mounted to a round bottomed flask with a capacity of 300 ml. To this round-bottomed flask were added:

(a) 100 ml (107 g) of o-toluic acid methyl ether, (b) 0.225 g (1 mmole) of palladium acetate $(Pd(OAc)_2)$, (c) 0.297 g (1.5 mmoles) of 1,10-phenanthroline-hydrate $(phen.H_2O)$, and (d) 0.200 g (1 mmole) of copper acetatehydrate $(Cu(OAc_2.H_2O)$ to prepare a reaction mixture.

The reaction mixture in the above-mentioned round-bottomed flask was heated on an oil bath at a reaction temperature of 200° C., air was blown into the above-mentioned reaction mixture from the gas blowing pipe at a feed rate of 300 ml/min (under the ambient atmospheric pressure), to bubble the reaction mixture, and the oxidative coupling reaction was carried out at the above-mentioned reaction temperature for 15 hours.

After the above-mentioned reaction was completed, a gas chromatographic analysis was applied to the reaction product in the reaction mixture. As a result, it was confirmed that the reaction contained 5.91 g of the compound of the chemical formula (P), 5.88 g of the compound of the chemical formula (Q), 1.30 g of the compound of the chemical formula (R), and 0.66 g of other dimer compounds.

The compounds of the above-mentioned formulae were subjected to measurements of the amount thereof, the yield based on the starting materials, and the yield based on the amount of palladium. The results are shown in Table 2.

Operation of Isolation of Various Reaction Products

The above-mentioned reaction mixture was subjected to a reduced pressure distillation. First, o-toluic acid methyl ester remaining after the distillation was recovered at 60° to 90° C. under a pressure Kp2 (a reduced pressure of 2 Torr), then 0.90 g of a fraction at 90° to 195° C. under Kp1 (a reduced pressure of 1 Torr), 12.5 g of a fraction at 195 to 205° C. under Kp1, and 1.5 g of high boiling point residue were obtained.

A. Isolation of Compound of Formula (P)

12.5 g of the fraction recovered at 195° to 205° C. under Kp1 was added with 30 ml of methanol, heat dissolved, then the solution was filtered in a heated state (filtered during heating) to recover 3.5 g of component insoluble in heated methanol. This recovered product was recrystallized with ethanol to isolate 3.0 g of needle shaped white crystals (melting point: 134° to 135° C.). The needle shaped white crystals isolated in the above-mentioned way were subjected to $^1H$ NMR ($CDCl_3$) analysis, mass analysis, and IR analysis. As a result, it was confirmed that the isolated compound was 3,3'-dimethyl-biphenyl-4,4-dicarboxylic acid dimethyl ester (the chemical formula (P)).

$^1H$ NMR analysis charts of the compound of the above-mentioned formula (P) are shown in FIG. 7(a) and FIG. 7(b). The mass analysis charts are shown in FIG. 8(a) and FIG. 8(b), while the IR analysis chart is shown in FIG. 9.

The peaks in the $^1H$ NMR analysis charts of the compound of formula (P), shown in FIG. 7(a) and FIG. 7(b), were as follows:

$\delta = 2.68$ ppm (6H; $CH_3$)
$\delta = 3.92$ ppm (6H;$CO_2CH_3$)
$\delta = 7.48$ ppm (2H;$^6H$)
$\delta = 7.49$ ppm (2H;$^2H$)
$\delta = 8.01$ ppm (2H;$^5H$)
$J_{5,6} = 8.3$ Hz

B. Isolation of Compound of Formula (Q)

Next, the filtrate of the heat filtration mentioned above was cooled to room temperature to cause precipitation of 6.0 g of crystals (the mixing ratio of compounds of formulae (P):(Q):(R) being 31:62:6). The crystals were subjected to a plurality of recrystallizations by methanol to isolate 2.0 g of crystals (melting point: 90° to 91.5° C.). The crystals isolated as mentioned above were subjected to $^1H$ NMR($CDCl_3$) analysis, mass analysis, and IR analysis. As a result, it was confirmed that the isolated compound was 3,4'-dimethyl-biphenyl-4,3'-dicarboxylic acid dimethyl ester (formula (Q)).

The $^1H$ NMR analysis charts of the compound of the above-mentioned formula (Q) are indicated in FIG. 1(a) and FIG. 1(b), the mass analysis charts are indicated in FIG. 2(a) and FIG. 2(b), and the IR analysis chart is shown in FIG. 3.

The peaks in the $^1H$ NMR charts of the compound of the formula (Q) shown in FIG. 1 are as follows:

$\delta = 2.64$ ppm (3H;4'—$CH_3$)
$\delta = 2.68$ ppm (3H;3—$CH_3$)
$\delta = 3.92$ ppm (3H;4—$CO_2CH_3$)
$\delta = 3.93$ ppm (3H;3'—$CO_2Ch_3$)
$\delta = 7.33$ ppm (1H;$^{5'}H$)
$\delta = 7.47$ ppm (1H;$^6H$)
$\delta = 7.48$ ppm (1H;$^2H$)
$\delta = 7.65$ ppm (1H;$^6$ H)
$\delta = 8.00$ ppm (1H;$^5H$)
$\delta = 8.17$ ppm (1H;$^2$ H)
$J_{2',6'} = J_{6',2'} = 2.0$ Hz
$J_{6',5'} = J_{5',6'} = 7.8$ Hz
$J_{5,6} = 8.8$ Hz

C. Isolation of Compound of Formula (R)

The mother liquors formed in the above-mentioned recrystallizations were all collected and redistilled to obtain a fraction at 195° to 204° C. under Kpl. The fraction was subjected to a plurality of recrystallizations by methanol to isolate 0.3 g of crystal (melting point: 112° to 113° C.). The crystal isolated in this way was subjected to $^1$H NMR(CDCl$_3$) analysis, mass analysis, and IR analysis, and as a result, it was confirmed that the isolated compound was 4,4'-dimethyl-biphenyl-3,3'-dicarboxylic acid dimethyl ester (formula (R)).

The $^1$H NMR analysis charts of the compound of the above-mentioned formula (R) are shown in FIG. 4(a) and FIG. 4(b), the mass analysis charts are shown in FIG. 5(a) and FIG. 5(b), and the IR analysis chart is shown in FIG. 6.

The peaks of the $^1$H NMR analysis charts of the compound of the structural formula (R) shown in FIG. 4 are as follows:

$\delta = 2.64$ ppm (6H;CH$_3$)
$\delta = 3.93$ ppm (6H;CO$_2$Ch$_3$)
$\delta = 7.32$ ppm (2H;$^5$H)
$\delta = 7.64$ ppm (2H;$^6$H)
$\delta = 8.15$ ppm (2H;$^2$H)
$J_{2,6} = J_{6,2} = 2.3$ Hz
$J_{6,5} = J_{5,6} = 8.2$ Hz The results of elementary analysis of the dimethyl-biphenyl dicarboxylic acid dimethyl esters of the above-mentioned formulae (Q), (R), and (P) are shown in Table 1.

TABLE 1

| | Carbon | Hydrogen |
|---|---|---|
| Calculated value | 72.47 | 6.08 |
| Formula (P) | 72.36 | 6.03 |
| Formula (Q) | 72.53 | 6.04 |
| Formula (R) | 72.51 | 6.07 |

Example 2

The same procedures as in Example 1 were carried out except that the oxidative coupling reaction time was changed to eight hours.

The yields, yield rate, etc. of the resultant reaction product are shown in Table 2.

Example 3

The same procedures as in Example 2 were carried out except that, in the oxidative coupling reaction, the amount of the 1,10-phenanthroline-hydrate (phen.H$_2$O) used was changed to 0.238 g (1.2 mmoles).

The yields, yield rate, etc. of the resultant reaction product are shown in Table 2.

Example 4

The same procedures as in Example 1 were carried out except that the types and amounts of the components of the catalyst were changed to 0.112 g (0.5 mmole) of palladium acetate (Pd(OAc)$_2$), 0.099 g (0.5 mmole) of 1,10-phenanthroline-hydrate (phen.H$_2$O), and 0.181 g (0.5 mmole) of a chelate compound of copper acetate with 1,10-phenanthroline (phen.Cu(OAc)$_2$).

The yields, yield rate, etc. of the resultant reaction product are shown in Table 2.

Example 5

The same procedures as in Example 1 were carried out except that a mixture of 0.411 g (1 mmole) of a chelating product of palladium nitrate with 1,10-phenanthroline (phen-Pd(NO$_3$)$_2$) and 0.299 g (1.5 mmole) of copper acetate-hydrate (Cu(OAc)$_2$.H$_2$O) was used, as an oxidative coupling reaction catalyst, the oxidative coupling reaction temperature was changed to 205° C., and the reaction time was changed to eight hours.

The yields, yield rate, etc. of the resultant reaction product are shown in Table 2.

Example 6

The same procedures as in Example 5 were carried out except that a mixture of 0.225 g (1 mmole) of palladium acetate (Pd(OAc)$_2$), 0.200 g (1.0 mmole) of 1,10-phenanthroline-hydrate (phen.H$_2$O), and 0.368 g (1.0 mmole) of a chelating product of copper nitrate with 1,0-phenanthroline (phen.Cu(NO$_3$)$_2$) was used as an oxidative coupling reaction catalyst.

The yields, yield rate, etc. of the resultant reaction product are shown in Table 2.

Example 7

The same procedures as in Example 1 were carried out except that 0.312 g (2 mmoles) of $\alpha,\alpha'$-bipyridine was used as a bidentate ligand compound, and the reaction time was five hours.

The yields, yield rate, etc. of the resultant obtained reaction product are shown in Table 2.

Example 8

A stainless steel autoclave with a capacity of 270 ml was charged with a reaction mixture containing:

(a) 56 ml (60 g) of o-toluic acid methyl ester,
(b) 0.067 g (0.3 mmole) of palladium acetate (Pd(OAc)$_2$), and
(c) 0.097 g (0.3 mmole) of 1,10-phenanthroline-hydrate (phen.H$_2$O)

Compressed air was fed into the above-mentioned autoclave to pressurize the system to 50 atmospheres, the temperature of the reaction mixture was raised to a reaction temperature of 200° C., and the oxidative coupling reaction was performed at this reaction temperature by heating for five hours.

The yields, yield rate, etc. of the resultant reaction product are shown in Table 2.

Example 9

A four-neck flask with a capacity of one liter was charged with a reaction mixture containing:

(a) 500 ml (535 g) of o-toluic acid methyl ester,
(b) 1.123 g (5 mmoles) of palladium acetate (Pd(OAc)$_2$),
(c) 1.487 g (7.5 mmoles) of 1,10-phenanthroline-hydrate (phen.H$_2$O), and
(d) 0.998 g (5mmoles) of copper acetatehydrate (Cu(OAc)$_2$.H$_2$O)

The reaction mixture in the above-mentioned four-necked flask was heated on an oil bath at the reaction temperature of 200° C., then air was blown into and bubbled in the above-mentioned reaction mixture at a feed rate of 1 liter/min (the ambient atmospheric pressure), and the oxidative coupling reaction was performed at the above-mentioned reaction temperature for nine hours.

The yields, yield rate, etc. of the resultant reaction product are shown in Table 2.

Comparative Example 1

The same procedures as in Example 1 were carried out except that in the oxidative coupling reaction, no 1,10-phenanthroline-hydrate (phen.$H_2O$) was used.

The yields, yield rate, etc. of the resultant -/ reaction product are shown in Table 2.

Comparative Example 2

The same procedures as in Example 8 were carried out except that, in the oxidative coupling reaction, no 1,10-phenanthroline-hydrate (phen.$H_2O$) was used.

The yields, yield rate, etc. of the resultant reaction product are shown in Table 2.

Example 10

Oxidative Coupling Reaction

A reflux condenser, thermometer, agitator, and gas blowing pipe were mounted on a four-neck flask with a capacity of 3 liters, and to this four-necked flask was added a reaction mixture containing: ester, (a) 1500 ml (1605 g) of o-toluic acid methyl ester, (b) 3.368 g (15 mmoles) of palladium acetate ($Pd(OAc)_2$), (c) 4.163 g (21 mmoles) of 1,10-phenanthroline-hydrate (phen.$H_2O$) and (d) 2.995 g (15 mmoles) of copper acetatehydrate ($Cu(OAc)_2 \cdot H_2O$).

The reaction mixture in the above-mentioned four-necked flask was heated on an oil bath at a reaction temperature of 200° C., air was blown into the above-mentioned reaction mixture through the gas blowing pipe at a feed rate of 1 liter/min (the ambient atmospheric pressure), and the oxidative coupling reaction of the reaction mixture was carried out at the above-mentioned reaction temperature of 200° C. for nine hours while bubbling and agitating the reaction mixture at a rotational speed of 500 rpm.

TABLE 2

| Ex. No. | Am't of o-toluic acid methyl ester used (ml (g)) | Am't of catalysts used Pd salts g (m mole) | Am't of catalysts used Bidentate ligand g (m mole) | Am't of catalysts used Cu salts g (m mole) | Reaction temp. (°C.) | Reaction time (hr) | Reaction pressure (atm) |
|---|---|---|---|---|---|---|---|
| 1 | 100 (107) | $Pd(OAc)_2$ 0.225 (1) | phen.$H_2O$ 0.297 (1.5) | $Cu(OAc)_2.H_2O$ 0.200 (1.0) | 200 | 15 | (*)$_1$ |
| 2 | 100 (107) | $Pd(OAc)_2$ 0.225 (1) | phen.$H_2O$ 0.297 (1.5) | $Cu(OAc)_2.H_2O$ 0.200 (1.0) | 200 | 8 | (*)$_1$ |
| 3 | 100 (107) | $Pd(OAc)_2$ 0.225 (1) | phen.$H_2O$ 0.238 (1.2) | $Cu(OAc)_2.H_2O$ 0.200 (1.0) | 200 | 8 | (*)$_1$ |
| 4 | 100 (107) | $Pd(OAc)_2$ 0.112 (0.5) | phen.$H_2O$ 0.099 (0.5) | phen-$Cu(OAc)_2$ 0.181 (0.5) | 200 | 15 | (*)$_1$ |
| 5 | 100 (107) | phen.$Pd(NO_3)_2$ 0.411 (1) | | $Cu(OAc)_2.H_2O$ 0.299 (1.5) | 205 | 8 | (*)$_1$ |
| 6 | 100 (107) | $Pd(OAc)_2$ 0.225 (1) | phen.$H_2O$ 0.200 (1.0) | phen-$Cu(NO_3)_2$ 0.368 (1.0) | 205 | 8 | (*)$_1$ |
| 7 | 100 (107) | $Pd(OAc)_2$ 0.225 (1) | bipy 0.312 (2.0) | $Cu(OAc)_2.H_2O$ 0.200 (1.0) | 200 | 5 | (*)$_1$ |
| 8 | 56 (60) | $Pd(OAc)_2$ 0.067 (0.3) | phen.$H_2O$ 0.059 (0.3) | — | 200 | 5 | 50 |
| 9 | 500 (535) | $Pd(OAc)_2$ 1.123 (5.0) | phen.$H_2O$ 1.487 (7.5) | $Cu(OAc)_2.H_2O$ 0.998 (5.0) | 200 | 9 | (*)$_1$ |
| Comp. 1 | 100 (107) | $Pd(OAc)_2$ 0.225 (1) | — | $Cu(OAc)_2.H_2O$ 0.200 (1.0) | 200 | 15 | (*)$_1$ |
| Comp. 2 | 56 (60) | $Pd(OAc)_2$ 0.067 (0.3) | — | | 200 | 5 | 50 |

| | Reaction products in reaction solution | | | | | | | | | | |
|---|---|---|---|---|---|---|---|---|---|---|---|
| | Compounds of formula (P) | | | Compounds of formula (Q) | | | Compounds of formula (R) | | | Other dimers | | |
| Ex. No. | Amount g | Yield Material (*)$_2$ | % Pd (*)$_3$ | Amount g | Yield Material (*)$_2$ | % Pd (*)$_3$ | Amount g | Yield Material (*)$_2$ | % Pd (*)$_3$ | Amount g | Yield Material (*)$_2$ | % Pd (*)$_3$ |
| 1 | 5.91 | 5.52 | 1980 | 5.88 | 5.50 | 1970 | 1.30 | 1.21 | 440 | 0.66 | 0.62 | 220 |
| 2 | 3.19 | 2.98 | 1070 | 3.17 | 2.96 | 1060 | 0.71 | 0.66 | 240 | 0.45 | 0.42 | 150 |
| 3 | 3.15 | 2.94 | 1060 | 3.15 | 2.94 | 1060 | 0.70 | 0.65 | 290 | 0.44 | 0.41 | 150 |
| 4 | 4.54 | 4.24 | 3050 | 4.51 | 4.21 | 3030 | 0.99 | 0.93 | 660 | 0.81 | 0.76 | 540 |
| 5 | 2.64 | 2.47 | 890 | 2.63 | 2.46 | 880 | 0.59 | 0.55 | 200 | 0.55 | 0.51 | 180 |
| 6 | 3.84 | 3.59 | 1290 | 3.49 | 3.26 | 1170 | 0.89 | 0.83 | 300 | 0.52 | 0.49 | 170 |
| 7 | 0.68 | 0.64 | 230 | 1.27 | 1.19 | 430 | 0.45 | 0.42 | 150 | 0.37 | 0.35 | 120 |
| 8 | 0.23 | 0.38 | 230 | 0.20 | 0.33 | 200 | 0.05 | 0.33 | 50 | 0.03 | 0.05 | 30 |
| 9 | 26.03 | 4.87 | 1750 | 21.83 | 4.08 | 1470 | 6.03 | 1.13 | 400 | 3.07 | 0.57 | 210 |
| Comp. 1 | 0.004 | 0.004 | 1 | 0.033 | 0.031 | 11 | 0.032 | 0.030 | 10 | 0.346 | 0.32 | 116 |
| Comp. 2 | 0.003 | 0.005 | 3 | 0.018 | 0.03 | 20 | 0.017 | 0.030 | 19 | 1.548 | 2.58 | 1732 |

Notice:
(*)$_1$ The ambient atmospheric pressure
(*)$_2$ The term "Yield Material" refers to a molar ratio of the resultant product to starting material used.
(*)$_3$ The term "% Pd" refers to a molar ratio of the resultant product to Pb in catalyst used.

A gas chromatographic analysis was applied to the reaction product in the reaction mixture, and it was confirmed that the reaction product contained the following compounds:

| | |
|---|---|
| Compound of formula (P): | 83.39 g |
| Compound of formula (Q): | 68.07 g |
| Compound of formula (R): | 18.72 g and |
| Other dimer compounds: | 12.22 g |

Isolation procedures of Reaction Products

The above-mentioned reaction mixture was subjected to a reduced pressure distillation. First, the o-toluic acid methyl ester remaining in the reaction mixture was recovered, and then a distillation operation was further continued to obtain 10.9 g of a fraction at 90° to 190° C. under Kpl, 173.6 g of a main fraction at 190° to 215° C. under Kpl, and 32.6 g of high boiling point residue.

A. Isolation of Compound of Formula (P)

The 173.6 g of the main fraction obtained at 190° to 215° C. under Kpl was heat-dissolved in 250 ml of ethyl acetate, the solution was cooled to cause crystals to be precipitated, the precipitated crystals were filtered to recover the precipitate and, the precipitate was subjected to repeated recrystallization procedures by using ethyl acetate, and thus 28 g of needle shaped white crystals (P crystals, melting point: 134° to 135° C.) were isolated.

The needle shaped white crystals P crystals isolated in the above-mentioned way were subjected to the $^1$H NMR (CDCl$_3$) analysis, mass analysis, and IR analysis. As a result, it was confirmed that the P crystals was 3,3'-dimethyldiphenyl-4,4-dicarboxylic acid dimethyl ester (the chemical formula (P)).

B. Isolation of Compound of Formula (Q)

Next, the recrystallization filtrate of the abovementioned cooled ethyl acetate solution was concentrated, then subjected to repeated recrystallization procedures by using methanol to cause a precipitation of 18 g of white crystals (Q crystals, melting point: 90° to 91.5° C.).

The Q crystals were subjected to the $^1$H NMR(CDCl$_3$) analysis, mass analysis, and IR analysis. As a result, it was confirmed that the Q crystals was 3,4'-dimethyl-biphenyl-4,3'-dicarboxylic acid dimethyl ester (formula (Q)).

C. Isolation of Compound of Formula (R)

The mother liquors formed in the recrystallization procedures of the crystals of the formula (Q) were all collected and concentrated, then redistilled to obtain a fraction at 220° to 240° C. under Kp7. The fraction was subjected to repeated recrystallization procedures by using methanol to isolate 2.5 g of white crystals (R crystals, melting point: 112° to 113° C.).

The R crystals isolated in the above-mentioned way were subjected to the $^1$H-NMR(CDCl$_3$) analysis, mass analysis, and IR analysis, and as a result, it was confirmed that the R crystals was 4,4'-dimethyl-biphenyl-3,3'-dicarboxylic acid dimethyl ester (formula (R)).

Example 11

Ten g of the P crystals (compound of formula (P)) produced in Example 10 were mixed to 25 ml of n-butanol in a flask with an inner capacity of 500 ml. The mixture was heated to uniformly dissolve it, then an aqueous solution containing 3.22 g of caustic soda dissolved in 50 ml of water was added to the solution. The reaction mixture was heated for one hour with refluxing to hydrolyze the P crystal compound.

Thereafter, a Claisen head was attached to the above-mentioned flask containing the hydrolyzed product and, the hydrolyzed product was subjected to distillation for two hours while feeding distilled water to the flask, to distill away the n-butanol and 300 ml of water.

Further, the reaction solution in the above-mentioned flask was filtered under heating and distilled water was added to adjust the total volume thereof to 400 ml, then 13 ml of concentrated hydrochloric acid was added to acidify the solution, whereupon white precipitate was produced. This precipitate-containing solution was boiled, then the precipitate was separated out by filtration. The precipitate was repeatedly washed with hot water, until no chlorine ions could any longer be detected in the precipitate by using silver nitrate. Finally, the sufficiently washed precipitate was dried. The dried precipitate (crystal compound of formula (Pa)) was obtained in an amount of 8.85 g (yield: 97%).

The Pa crystal compound was subjected to the $^1$H NMR(DMF-d7) analysis, mass analysis (EI-MS), and IR analysis. As a result, the $^1$H NMR analysis charts shown in FIG. 10(a), FIG. 10(b), and FIG. 10(c), the mass analysis charts shown in FIG. 11(a) and FIG. 11(b), and the IR analysis chart shown in FIG. 12 were obtained. From these analysis results, it was confirmed that the Pa crystal compound was 3,3'-dimethyl-biphenyl-4,4'-dicarboxylic acid (compound of formula (Pa), melting point: 340° to 346° C.).

Note that the peaks shown in the above-mentioned $^1$H NMR(DMF-d7) analysis charts were as follows:

$\delta = 2.69$ ppm (6H, CH$_3$)
$\delta = 7.73$ ppm (2H, $^6$H)
$\delta = 7.77$ ppm (2H, $^2$H)
$\delta = 8.06$ ppm (2H, $^5$H)
$\delta = 13.23$ ppm (2H, COOH)
$J_{5,6} = 8.3$ Hz Example 12

The same procedures as in Example 11 were carried out except that in the 300 ml capacity flask, 3 g of the Q crystal (formula Q) produced in Example 10 were mixed with 10 ml of n-butanol, the mixture was heated to uniformly dissolve, then an aqueous solution obtained by dissolving 1.0 g of caustic soda in 20 ml of water was added, and this reaction mixture was refluxed for one hour to hydrolyze the crystal compound of formula Q. As a result of purification, 2.62 g of precipitate (white crystals of compound of formula (Qa)) were obtained (yield: 96%).

The white crystals (crystals of compound of formula (Qa)) were subjected to the $^1$H NMR analysis, mass analysis, and IR analysis, whereupon the charts shown in FIG. 13(a), FIG. 13(b), FIG. 13(c), FIG. 14(a), FIG. 14(b), and FIG. 15 were obtained, and as a result, it was confirmed that the above-mentioned Qa white crystal compounds consisted of 3,4'-dimethylbiphenyl-4,3'-dicarboxylic acid (compound of formula (Qa), melting point 312° to 315° C.).

Note that the peaks shown in the above-mentioned $^1$H NMR(DMF-d7) analysis charts were as follows:

$\delta = 2.65$ ppm (3H, 4'—CH$_3$)
$\delta = 2.70$ ppm (3H, 3—CH$_3$)

δ=7.47 ppm (1H, 5'H)
δ=7.68 ppm (1H, 6H)
δ=7.72 ppm (1H, 2H)
δ=7.88 ppm (1H, 6'H)
δ=8.07 ppm (1H, 5H)
δ=8.29 ppm (1H, 2'H)
δ=13.29 ppm (2H, COOH)
$J_{6',2'}=J_{2',6'}=1.5$ Hz
$J_{6',5'}=J_{5',6'}=8.3$ Hz
$J_{5,6}=7.8$ Hz Example 13

The same procedures as in Example 11 were carried out except that 2 g of R crystals produced in Example 10 (compound of formula (R)) were mixed with 7 ml of n-butanol in a flask of an inner capacity of 100 ml. The mixture was heated to uniformly same dissolve. To the resultant solution was added an aqueous solution obtained by dissolving 0.65 g of caustic soda in 20 ml of water, and this mixture was refluxed for one hour to hydrolyze the R crystal compound. A purification operation was performed to obtain 1.74 g of precipitate (white crystals of formula (Ra)) (yield rate of 96 percent). The Ra crystal compound was subjected to the 1H NMR analysis, mass analysis, and IR analysis, and as a result, the charts shown in FIG. 16(a), FIG. 16(b), FIG. 16(c), FIG. 17(a), FIG. 17(b), and FIG. 18 were obtained. From the analysis results, it was confirmed that the above-mentioned Ra crystal compound consisted of 4,4'-dimethyl-biphenyl-3,3'-dicarboxylic acid (compound of formula (Ra), melting point: 334° to 338° C.).

Note that the peaks shown in the above-mentioned 1H NMR(DMF-d7) analysis charts were as follows:
δ=2.64 ppm (6H, CH3)
δ=7.46 ppm (2H, 5H)
δ=7.83 ppm (2H, 6H)
δ=8.24 ppm (2H, 2H)
δ=13.31 ppm (2H, COOH)
$J_{2,6}=J_{6,2}=2.0$ Hz
$J_{6,5}=J_{5,6}=7.8$ Hz Example 14

4.0 g of the 3,3'-dimethyl-biphenyl-4,4'-dicarboxylic acid (compound of formula (Pa)) produced in Example 11 was heated with refluxing for 10 hours, together with 20 ml of thionyl chloride, to prepare a uniform solution, then the thionyl chloride was distilled out of the solution to leave a residue of white solid. The white solid was recrystallized from methylene chloride to provide 3.63 g of white solid (Pc crystal) (yield: 80%).

The white solid (Pc crystal) was subjected to the 1H NMR analysis, mass analysis, and IR analysis, whereupon the charts shown in FIG. 19(a), FIG. 19(b), FIG. 20(a), FIG. 20(b), and FIG. 21 were obtained. From the results of analysis, it was confirmed that the above-mentioned white solid (Pc crystal) consisted of 3,3'-dimethyl-biphenyl-4,4'-dicarboxylic acid dichloride (compound of formula (Pc), melting point: 190° to 193° C.).

Note that the peaks shown in the 1H NMR(CDCl3) analysis charts were as follows:
δ=2.67 ppm (6H, CH3)
δ=7.54 ppm (2H, 2H)
δ=7.59 ppm (2H, 6H)
δ=8.34 ppm (2H, 5H)
$J_{5,6}=J_{6,5}=8.3$ Hz

EXAMPLE 15

The same procedures as in Example 14 were carried out except that 2.0 g of the 3,4'-dimethyl-biphenyl-4,3'-dicarboxylic acid (compound of formula (Qa)) produced in Example 12 was refluxed for 10 hours together with 10 ml of thionyl chloride to prepare a homogeneous solution. As a result of a purification operation, 1.52 g of white solid (Qc crystals) were obtained (yield: 67%).

The white solid (Qc crystals) was subjected to the 1H NMR analysis, mass analysis, and IR analysis. As a result, the charts shown in FIG. 22(a), FIG. 22(b), FIG. 23(a), FIG. 23(b), and FIG. 24 were obtained. From the results of analysis, it was confirmed that the above-mentioned white solid (Qc crystals) consisted of 3,4'-dimethyl-biphenyl-4,3'-dicarboxylic acid dichloride (compound of formula (Qc), melting point: 140° to 144° C.).

Note that the peaks shown in the 1H NMR(CDCl3) analysis charts were as follows:
δ=2.63 ppm (3H, 4'—CH3)
δ=2.67 ppm (3H, 3—CH3)
δ=7.42 ppm (1H, 5H)
δ=7.52 ppm (1H, 2H)
δ=7.58 ppm (1H, 6H)
δ=7.77 ppm (1H, 6'H)
δ=8.20 ppm (1H, 5H)
δ=8.45 ppm (1H, 2'H)
$J_{2',6'}=J_{6',2'}=1.5$ Hz
$J_{6',5'}=J_{5',6'}=7.8$ Hz
$J_{6,5}=J_{5,6}=8.3$ Hz Example 16

The same procedures as in Example 14 were carried out except that 1.0 g of the 4,4'-dimethyl-biphenyl-3,3-dicarboxylic acid (Ra) produced in Example 13 was refluxed with 5 ml of thionyl chloride for 10 hours to provide a homogeneous solution. As a result of a purification operation, 0.77 g of white solid (crystal of formula (Rc)) was obtained (yield: 68%).

The white solid (Rc crystals) was subjected to the 1H NMR analysis, mass analysis, and IR analysis. As a result, the charts shown in FIG. 25(a), FIG. 25(b), FIG. 26(a), FIG. 26(b), and FIG. 27 were obtained. From the results of analysis, it was confirmed that the above-mentioned white solid (Rc crystals) consisted of 4,4'-dimethyl-biphenyl-3,3'-dicarboxylic acid dichloride (compound of formula (Rc), melting point: 169° to 171° C.).

Note that the peaks shown in the 1H NMR(CDCl3) analysis charts were as follows:
δ=2.63 ppm (6H, CH3)
δ=7.42 ppm (2H, 5H)
δ=7.75 ppm (2H, 6H)
δ=8.42 ppm (2H, 2H)
$J_{2,6}=J_{6,2}=2.0$ Hz
$J_{6,5}=J_{5,6}=7.8$ Hz The results of the elementary analysis on the compounds obtained in the above-mentioned Examples 11 to 16 are shown in Table 3 and Table 4.

TABLE 3

| | Dicarboxylic Acid Compounds of Formulae (Pa), (Qa), and (Ra) | |
|---|---|---|
| | C | H |
| Calculated value | 71.10 | 5.22 |
| Compound Pa | 71.18 | 5.31 |

TABLE 3-continued

| Dicarboxylic Acid Compounds of Formulae (Pa), (Qa), and (Ra) | | |
|---|---|---|
| | C | H |
| Calculated value | 71.10 | 5.22 |
| Compound Qa | 71.20 | 5.37 |
| Compound Ra | 70.70 | 5.36 |

TABLE 4

| Acid Chloride Compounds of Formulae (Pc), (Qc), and (Rc) | | | |
|---|---|---|---|
| | C | H | Cl |
| Calculated value | 62.56 | 3.94 | 23.08 |
| Compound Pc | 62.85 | 4.02 | 23.11 |
| Compound Qc | 62.70 | 3.86 | 23.15 |
| Compound Rc | 62.45 | 4.00 | 23.13 |

CAPABILITY OF EXPLOITATION IN INDUSTRY

In the process of the present invention, an oxidative coupling reaction of o-toluic acid alkyl ester enables the production of 3,4,3', 4'-substituted dimethyl biphenyl dicarboxylic acid dialkyl ester with a high selectivity of at least 80 mol % and with a high yield of at least 500 molar % based the molar amount of the palladium salts contained in the catalyst used. This 3,4,3',4'-substituted dimethyl biphenyl dicarboxylic acid and its acid chlorides. These dicarboxylic acid compounds and dicarboxylic acid dichloride compounds can be used to produce useful polyesters or polyamides by a polymerization thereof with various types of diol compounds or diamine compounds.

We claim:

1. A process for producing a 3,4,3',4'-substituted biphenyl compound comprising the step of:

oxidatively coupling an o-toluic acid alkyl ester represented by the formula (I):

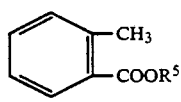

in which $R^5$ represents an alkyl group having 1 to 5 carbon atoms, in the presence of a catalyst containing at least one member selected from the group consisting of a mixture of at least one palladium salt with at least one member selected from the group consisting of 1,10-phenanthroline and α,α'-bipyridine, in an amount of 0.9 to 4 times the molar amount of the palladium salt, a chelating product of a palladium salt with 1,10-phenanthroline, and a chelating product of a palladium salt with α,α'-bipyridine, in an atmosphere containing molecular oxygen, to selectively produce a dimethyl biphenyl dicarboxylic acid dialkyl ester having two methyl groups and two alkoxy carbonyl groups substituted at 3, 4, 3', and 4'-positions of the biphenyl ring structure, to prepare a compound represented by the formula (II):

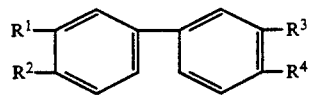

wherein, one of $R^1$ and $R^2$ represents a —$CH_3$ group and the other one thereof represents a —$COOR^5$ group, wherein $R^5$ is the same as previously defined, and one of $R^3$ and $R^4$ represents a —$CH_3$ group and the other one thereof represents a —$COOR^5$ group, wherein $R^5$ is the same as previously defined.

2. The process as set forth in claim 1, wherein the palladium salt is selected from the group consisting of a palladium salt of an aliphatic carboxylic acid having 1 to 5 carbon atoms, a palladium salt of hydrochloric acid, nitric acid, nitrous acid, sulfuric acid, sulfurous acid, and phosphoric acid, and a palladium-chelated salt of a β-diketone compound.

3. The process as set forth in claim 1, wherein the catalyst further contains at least one type of copper salt.

4. The process as set forth in claim 3, wherein the copper salt is selected from the group consisting of a copper salt of an aliphatic carboxylic acid having 1 to 5 carbon atoms, a copper salt of hydrochloric acid, nitric acid, nitrous acid, sulfuric acid, sulfurous acid, and phosphoric acid, and a copper-chelated salt of a β-diketone compound.

5. The process as set forth in claim 1, wherein the catalyst is used in an amount of 0.0001 to 0.1 mole, in terms of the palladium salt, per mole of o-toluic acid alkyl ester.

6. The process as set forth in claim 3, wherein the copper salt is used in an amount of 0.01 to 10 moles per mole of the a palladium salt.

7. The process as set forth in claim 1, wherein the oxidation coupling reaction is carried out at a temperature of 50° to 300° C. and under a pressure of from ambient atmospheric pressure to 300 atmospheres.

8. The process as set forth in claim 1, wherein the molecular oxygen-containing atmosphere has an oxygen partial pressure of 0.05 to 10 atmospheres.

9. The process as set forth in claim 1, wherein the biphenyl compound of formula (II) is produced at a selectivity of 80% or more.

10. The process as set forth in claim 1, further comprising the step of isolating (1) a biphenyl compound of the formula (II) in which $R^1$ and $R^4$ both represent a —$CH_3$ group and $R^2$ and $R^3$ both represent a —$COOR^5$ group and (2) a biphenyl compound of the formula (II) in which $R^1$ and $R^3$ both represent a —$COOR^5$ group and $R^2$ and $R^4$ both represent a —$CH_3$ group, from the oxidative coupling reaction product.

11. The process as set forth in claim 1, further comprising the step of isolating a biphenyl compound of the formula (II) wherein $R^1$ and $R^3$ both represent a —$CH_3$ group and $R^2$ and $R^4$ both represent a —$COOR^5$ group, from the oxidative coupling reaction product.

12. The process as set forth in claim 1, further comprising the step of hydrolyzing the resultant dimethyl biphenyl dicarboxylic acid dialkyl ester by modifying the —$COOR^5$ groups in the formula (II) to —COOH groups to produce the corresponding dimethyl biphenyl dicarboxylic acid.

13. The process as set forth in claim 12, further comprising the step of isolating a biphenyl compound of the formula (II), wherein $R^1$ and $R^4$ both represent a —$CH_3$ group and $R^2$ and $R^3$ both represent a —COOH group, from the oxidative coupling reaction product.

14. The process as set forth in claim 12, further comprising the step of isolating a biphenyl compound of the formula (II), wherein $R^2$ and $R^4$ both represent a —$CH_3$ group and $R^1$ and $R^3$ both represent a —COOH group, from the oxidative coupling reaction product.

15. The process as set forth in claim 12, further comprising the step of chloridizing the resultant dimethyl biphenyl dicarboxylic acid by modifying the —COOH groups to —COCl groups to product the corresponding dimethyl biphenyl dicarboxylic acid chloride.

16. The process as set forth in claim 15, wherein the dimethyl biphenyl dicarboxylic acid dichloride is produced by a reaction of the dimethyl biphenyl dicarboxylic acid with a chloridization agent containing at least one member selected from the group consisting of phosphorus trichloride, phosphorus pentachloride, and thionyl chloride.

17. The process as set forth in claim 15, further comprising the step of isolating a biphenyl compound of the formula (II), wherein $R^1$ and $R^4$ both represent a —$CH_3$ group and $R^2$ and $R^3$ both represent a —COCl group, from the oxidative coupling reaction product.

18. The process as set forth in claim 15, further comprising the step of isolating a biphenyl compound of the formula (II), wherein $R^2$ and $R^4$ both represent a —$CH_3$ group and $R^1$ and $R^3$ both represents a —COCl group, from the oxidative coupling reaction product.

* * * * *

UNITED STATES PATENT AND TRADEMARK OFFICE
CERTIFICATE OF CORRECTION

PATENT NO. : 5,243,067
DATED : September 7, 1993
INVENTOR(S) : Akinori SHIOTANI et al.

It is certified that error appears in the above-indentified patent and that said Letters Patent is hereby corrected as shown below:

Title page, in the Abstract, line 13, delete "products" and insert --product--; and line 16, delete "esters" and insert --ester--.

Claim 1, column 19, line 54, before "a mixture" insert --(a)--;

line 58, before "a chelating product" insert --(b)--;

line 60, before "a chelating product" insert --(c)--; and

Claim 1, column 20, line 12, delete "Ch$_3$" and insert --CH$_3$--.

Claim 6, column 20, line 37, delete "a".

Claim 7, column 20, line 39, delete "oxidation" and insert --oxidative--.

UNITED STATES PATENT AND TRADEMARK OFFICE
CERTIFICATE OF CORRECTION

PATENT NO. : 5,243,067
DATED : September 7, 1993
INVENTOR(S) : Akinori SHIOTANI et al.

It is certified that error appears in the above-indentified patent and that said Letters Patent is hereby corrected as shown below:

Claim 15, column 21, line 12, delete "product" and insert --produce--.

Signed and Sealed this

Twenty-ninth Day of March, 1994

Attest:

BRUCE LEHMAN

Attesting Officer     Commissioner of Patents and Trademarks